(12) United States Patent
Steele et al.

(10) Patent No.: US 12,410,411 B2
(45) Date of Patent: Sep. 9, 2025

(54) BIOCATALYTIC TECHNIQUES

(71) Applicant: HYPHA DISCOVERY LIMITED, Abingdon (GB)

(72) Inventors: Jonathan Charles Paul Steele, Abingdon (GB); Antonio De Riso, Abingdon (GB); Francesco Falcioni, Manchester (GB); Stephen Keith Wrigley, Abingdon (GB); Emily Jade Hopkins, Abingdon (GB); Aksana Rimu Khan, Abingdon (GB); Kinga Linda Nytko, Abingdon (GB); Vincent Poon, Abingdon (GB); John Maxim Ward, London (GB); Sebastian Schulz, Schenkendöbern (DE)

(73) Assignee: HYPHA DISCOVERY LIMITED, Abingdon (GB)

( * ) Notice: Subject to any disclaimer, the term of this patent is extended or adjusted under 35 U.S.C. 154(b) by 541 days.

(21) Appl. No.: 17/778,315

(22) PCT Filed: Nov. 23, 2020

(86) PCT No.: PCT/GB2020/052982
§ 371 (c)(1),
(2) Date: May 19, 2022

(87) PCT Pub. No.: WO2021/099807
PCT Pub. Date: May 27, 2021

(65) Prior Publication Data
US 2023/0040326 A1    Feb. 9, 2023

(30) Foreign Application Priority Data
Nov. 22, 2019 (GB) .................................. 1917077

(51) Int. Cl.
| | |
|---|---|
| *C12N 9/02* | (2006.01) |
| *C12N 15/70* | (2006.01) |
| *C12P 7/26* | (2006.01) |
| *C12P 7/6409* | (2022.01) |
| *C12P 13/00* | (2006.01) |
| *C12P 13/02* | (2006.01) |
| *C12P 17/04* | (2006.01) |
| *C12P 17/10* | (2006.01) |
| *C12P 17/12* | (2006.01) |
| *C12P 17/16* | (2006.01) |
| *C12P 17/18* | (2006.01) |

(52) U.S. Cl.
CPC .......... *C12N 9/0071* (2013.01); *C12N 15/70* (2013.01); *C12P 7/26* (2013.01); *C12P 7/6409* (2013.01); *C12P 13/001* (2013.01); *C12P 13/02* (2013.01); *C12P 17/04* (2013.01); *C12P 17/10* (2013.01); *C12P 17/12* (2013.01); *C12P 17/16* (2013.01); *C12P 17/165* (2013.01); *C12P 17/167* (2013.01); *C12P 17/181* (2013.01); *C12P 17/182* (2013.01); *C12Y 114/14001* (2013.01)

(58) Field of Classification Search
CPC ......... C12N 9/0071; C12N 15/70; C12P 7/26; C12P 7/6409; C12P 13/001; C12P 13/02; C12P 17/04; C12P 17/10; C12P 17/12; C12P 17/16; C12P 17/165; C12P 17/167; C12P 17/181; C12P 17/182; C12Y 114/14001
See application file for complete search history.

(56) References Cited

U.S. PATENT DOCUMENTS

| | | | |
|---|---|---|---|
| 3,131,127 A | 4/1964 | Gaeumann et al. | |
| 6,884,608 B2 | 4/2005 | Basch et al. | |
| 8,293,979 B2 | 10/2012 | Nakajima et al. | |
| 2005/0084859 A1* | 4/2005 | Nakajima | C12N 15/8274 800/278 |
| 2010/0313300 A1 | 12/2010 | Nakajima et al. | |
| 2014/0038850 A1 | 2/2014 | Fasan et al. | |

FOREIGN PATENT DOCUMENTS

| | | |
|---|---|---|
| CN | 109022515 | 12/2018 |
| GB | 2580879 | 8/2020 |
| GB | 2581122 | 8/2020 |
| JP | 2004-57194 | 2/2004 |
| WO | 02/083062 | 10/2002 |
| WO | 02/092801 | 11/2002 |
| WO | 03/057830 | 7/2003 |
| WO | 2004/078978 | 9/2004 |

(Continued)

OTHER PUBLICATIONS

Livingstone CD, Barton GJ. Protein sequence alignments: a strategy for the hierarchical analysis of residue conservation. Comput Appl Biosci. Dec. 1993;9(6):745-56. doi: 10.1093/bioinformatics/9.6. 745. PMID: 8143162. (Year: 1993).*

(Continued)

*Primary Examiner* — Sharmila G Landau
*Assistant Examiner* — Natalie Iannuzo
(74) *Attorney, Agent, or Firm* — Wenderoth, Lind & Ponack, L.L.P.

(57) ABSTRACT

The present invention relates to a cytochrome P450 enzyme comprising the amino acid sequence set forth in SEQ ID NO: 3, or a variant thereof having an amino acid sequence having at least 95% identity thereto and having CYP450 activity. The cytochrome P450 enzyme provided herein was isolated from *Streptomyces eurythermus* NRRL 2539 and has a wide substrate range and high activity, and may be used to oxidate organic compounds.

13 Claims, 10 Drawing Sheets
Specification includes a Sequence Listing.

(56) References Cited

FOREIGN PATENT DOCUMENTS

| WO | 2011/038313 | | 3/2011 | | |
|---|---|---|---|---|---|
| WO | 2012/109586 | | 8/2012 | | |
| WO | 2013/073775 | | 5/2013 | | |
| WO | WO-2013073775 | A1 * | 5/2013 | ............ | A61K 38/17 |
| WO | 2016/007623 | | 1/2016 | | |
| WO | 2018/091885 | | 5/2018 | | |
| WO | 2019/220093 | | 11/2019 | | |
| WO | 2020/109776 | | 6/2020 | | |

OTHER PUBLICATIONS

Alexander Dennig, "Engineering of P450 Enzymes for Application in Phenol Synthesis", (2013), pp. 1-222.
Susan Lepri et al., "Metabolism Study and Biological Evaluation of Bosentan Derivative", Eur. J. Med. Chem., vol. 121, (2016), pp. 658-670.
Waldemar Adam et al., "Biocatalytic Asymmetric Hydroxylation of Hydrocarbons with the Topsoil-Microorganism Bacillus Megaterium", J. Org. Chem., vol. 65, (2000), pp. 878-882.
Rudi Fasan, "Tuning P450 Enzymes as Oxidation Catalysts", ACS Catal., vol. 2, (2012), pp. 647-666.
Laila Roper et al., "Biocatalysis for Organic Chemists: Hydroxylations" Organic Synthesis Using Biocatalysis, Chapter 8, (2016), pp. 213-241.
Annabelle Le Gal et al., "Diversity of Selective Environmental Substrates for Human P450 2A6: alkoxyethers, nicotine, coumarin, N-nitrosodiethylamine, and N-nitrosobenzylmethylamine", Toxicology Lett., vol. 144, (2003), pp. 77-91.
Antti Mantyla et al., "Synthesis and Antileishmanial Activity of Novel Buparvaquone Oxime Derivatives", Bioorg. Med. Chem., vol. 12, (2004), pp. 3497-3502.
Katsunori Nakamura et al., "Coumarin Substrates for Cytochrome P450 2D6 Fluorescence Assays", Anal. Biochem. vol. 292, (2001), pp. 280-286.
Appleby, "A Soluble haemoprotein P450 from nitrogen-fixing Rhizobium bacteroids", Biochim. Biophys. Acta, vol. 147, (1967), pp. 399-402.
D. A. Broadbent et al., "Bacterial attack on phenolic ethers Electron acceptor-substrate binding proteins in bacterial O-dealkylases: purification and characterization of cytochrome P450npd of Nocardia", Microbios., vol. 9, (1974), pp. 119-130.
P. B. Danielson, "The Cytochrome P450 Superfamily: Biochemistry, Evolution and Drug Metabolism in Humans", Current Drug Metabolism, vol. 3, (2002), pp. 561-597.
Israel Hanukoglu, "Electron Transfer Proteins of Cytochrome P450 Systems", Advances in Molecular and Cell Biology, vol. 14, (1996), pp. 29-56.
Haitham A. Hussain et al., "Enhanced Heterologous Expression of Two *Streptomyces griseolus* Cytochrome P450s and *Streptomyces coelicolor* Ferredoxin Reductase as Potentially Efficient Hydroxylation Catalysts", Applied and Environmental Microbiology, vol. 69, No. 1, (2003), pp. 373-382.
David C. Lamb et al., "The First Virally Encoded Cytochrome P450", Journal of Virology, vol. 83, No. 16, (2009), pp. 8266-8269.
Linda Owers Narhi et al., "Characterization of a Catalytically Self-sufficient 119,000-Dalton Cytochrome P-450 Monooxygenase Induced by Barbiturates in Bacillus megaterium", Journal of Biological Chemistry, vol. 261, No. 16, (1986), pp. 7160-7169.
F. Sima Sarlaslani et al., "Induction of cytochrome P-450 in *Streptomyces griseus*", Biochemical and Biophysical Research Communications, vol. 141, No. 2, (1986), pp. 405-410.
Herzl Schwalb et al., "Purification and characterization of pentobarbital-induced cytochrome P-450BM-1 from Bacillus megaterium ATCC 14581", Biochimica et Biophysica Acta, vol. 838, No. 3, (1985), pp. 302-311.
Ali Shafiee et al., "Macrolide Antibiotic Biosynthesis: Isolation and Properties of Two Forms of 6-Deoxyerythronolide B Hydroxylase from *Saccharopolyspora erythraea* (*Streptomyces erythreus*)", Biochemistry, vol. 26, No. 19, (1987), pp. 6204-6210.
Astrid Sigel et al., "The Ubiquitous Roles of Cytochrome P450 Proteins", Metal Ions in Life Sciences, vol. 3, (2007), pp. 1-667.
C-A. Yu et al., "Cytochrome P-450cam, Crystallization and Properties", Journal of Biological Chemistry, vol. 249, No. 1, (1974), pp. 94-101.
Jonathan Basch et al., "Cloning and expression of a cytochrome P450 hydroxylase gene from Amycolatopsis orientalis: hydroxylation of epothilone B for the production of epothilone F", J. Ind. Microbiol. Biotechnol., vol. 34, (2007), pp. 171-176.
Giovanna Di Nardo et al., "Optimization of the Bacterial Cytochrome P450 BM3 System for the Production of Human Drug Metabolites", Int. J. Mol. Sci., vol. 13, (2012), pp. 15901-15924.
Hazel M Girvan et al., "Applications of microbial cytochrome P450 enzymes in biotechnology and synthetic biology", Curr. Opin. Chem. Biol., vol. 31, (2016), pp. 136-145.
David C. Lamb et al., "Unusual properties of the cytochrome P450 superfamily", Phil. Transac. Royal Soc. B, (2013), pp. 1-13.
Suzy C. Moody et al., "CYP105-diverse structures, functions and roles in an intriguing family of enzymes in *Streptomyces*", J. Appl. Microbiol., vol. 117, No. 6, (2014), pp. 1549-1563.
Jeffrey D. Rudolf et al., "Cytochromes P450 for natural product biosynthesis in *Streptomyces*: sequence, structure, and function", Natural Product Reports, vol. 34, No. 9, (2017), pp. 1141-1172.
Keiko Hayashi et al., "Structure-based design of a highly active vitamin D hydroxylase from *Streptomyces griseolus* CYP105A1", Biochem., vol. 47, No. 46, (2008), pp. 11964-11972.
Hiroshi Sugimoto et al., "Crystal Structure of CYP105A1 (P450SU-1) in Complex with 1-alpha-25-Dihydroxyvitamin D3", Biochem., vol. 47, No. 13, (2008), pp. 4017-4027.
Kazuo Ohta et al., "Production of Human Metabolites of Cyclosporin A, AMI, AM4N and AM9, by Microbial Conversion", J. Biosci. Bioeng., vol. 99, No. 4, (2005), pp. 390-395.
Emma J. Sherwood et al., "Cloning and Analysis of the Planosporicin Lantibiotic Biosynthetic Gene Cluster of Planomonospora alba", J. Bacteriol., vol. 195, No. 10, (2013), pp. 2309-2321.
D. K. Summers et al., "Resolution of ColE1 dimers requires a DNA sequence implicated in the three-dimensional organization of the cer site", EMBO J., vol. 7, No. 3, (1988), pp. 851-858.
Julie D. Thompson et al., "Clustal W: improving the sensitivity of progressive multiple sequence alignment through sequence weighting, position-specific gap penalties and weight matrix choice", Nucl. Acids Res., vol. 22, No. 22, (1994), pp. 4673-4680.
Bingbing Ma et al., "Hydroxylation of Steroids by a Microbial Substrate-Promiscuous P450 Cytochrome (CYP105D7): Key Arginine Residues for Rational Design", Appl. Environ. Microbiol., vol. 85, No. 23, (2019), e01530-19, pp. 1-14.
Lian-Hua Xu et al., "Structural basis for the 4'-hydroxylation of diclofenac by a microbial cytochrome P450 monooxy genase", Appl. Microbiol. Biotech., (2014), DOI 10.1007/s00253-014-6148-y.
Qiuping Yao et al., "Hydroxylation of Compactin (ML-236B) by CYP105D7 (SAV_7469) from *Streptomyces avermitilis*", J. Microbiol. Biotech., (2017), vol. 27, No. 5, pp. 956-964.
Stephen G. Bell et al., "Engineering the CYP101 system for in vivo oxidation of unnatural substrates", Protein Eng., vol. 14, No. 10, (2001), pp. 797-802.
Hiroki Kabumoto et al., "Directed Evolution of the Actinomycete Cytochrome P450 MoxA (CYP105) for Enhanced Activity", Biosci. Biotechnol. Biochem., vol. 73, No. 9, (2009), pp. 1922-1927.
Ling Liu et al., "Hydroxylation of flavanones by Cytochrome P450 105D7 from *Streptomyces avermitilis*", J. Molec. Catalysis B: Enzymatic, vol. 132, (2016), pp. 91-97.
Kazuhiro Machida et al., "Increase in Pladienolide D Production Rate Using a *Streptomyces* Strain Overexpressing a Cytochrome P450 Gene", J. Biosci. Bioeng., vol. 105, No. 6, (2008), pp. 649-654.
UniProt: L8EFR2, "SubName: Full=Cytochrome P450-like enzyme {ECO:0000313/ EMBL: ELQ78055.1}", Apr. 3, 2012, XP002797538—cited in ISR/WO, copy not provided by the Searching Authority.
Office Action issued Jul. 18, 2024 in corresponding European Patent Application No. 20815909.5.

(56) References Cited

OTHER PUBLICATIONS

Office Action issued May 28, 2024 in Japanese Patent Application No. 2022-529649, with English-language Translation.
P. D. Millner, et al., "Microbially Mediated Growth Suppression and Death of *Salmonella* in Composted Sewage Sludge", Micro Ecol, 1987, vol. 14, pp. 255-265.
International Search Report and Written Opinion of the International Searching Authority issued Feb. 26, 2021, in International; (PCT) Application No. PCT/GB2020/052982.
Worsch, A. et al., "A novel cytochrome P450 mono-oxygenase from *Streptomyces platensis* resembles activities of human drug metabolizing P450s", Biotechnology and Bioengineering, vol. 115, No. 9, 2018, pp. 2156-2166.
Weber, J.M. et al., "Organization of a Cluster of Erythromycin Genes in *Saccharopolyspora erythraea*", Journal of Bacteriology, vol. 172, No. 5, 1990, pp. 2372-2383.
Sequence 137 from U.S. Pat. No. 8,293,979, issued Oct. 23, 2012; EBI accession No. USPOP:AFX15846, 2 pages.
Schell, U. et al., "Engineered biosynthesis of hybrid macrolide polyketides containing D-angolosamine and D-mycaminose moieties", Organic & Biomolecular Chemistry, 2008, vol. 6, pp. 3315-3327.

\* cited by examiner (a)

(b)

(c)

(d)

(e)

(f)

SEQUENCE LISTING

<160> NUMBER OF SEQ ID NOS: 17

<210> SEQ ID NO 1
<211> LENGTH: 1494
<212> TYPE: DNA
<213> ORGANISM: Streptomyces eurythermus

<400> SEQUENCE: 1

```
atgaagatcg gcacgacgca cctcactcgt ctgcgaggtc tttccatgac ggaactgacg      60
gacatcaccg gcccggctgc ccaggccgaa accgtcgcat tccccagga ccgcacctgt      120 ccctaccatc cccccaccgg atacgacccg ctgcgcgacg ggcgaccct gtcccgcgtc      180 accctctacg acggccgcga ggtctggctg gtcaccgccc aggccaccgc ccgcgccctg      240
ctcgccgacc cccggctgtc caccgaccgc cgccgcgacg gcttcccgt gcccacccc      300 cgcttcgcgc cggccgcga ccgcacgctg gccctgctcg ggctggacga ccccgaacac      360
caccggcagc gccggctgct catcccgtcg ttcaccctca aacgcgccac cgcacagcgc      420
ccctggatcc agcggatcgt cgacgaactg ctggacgcca tgatcgcccg ggggccggtc      480
gccgacctcg tgtccgcctt cgcgctgccc gtgccgtcca tggtcatctg cgaactgctc      540
ggcgtgccct acgccgacca cgagttcttc gaggaacagt cccgccggct gctgcgcggc      600
ccgaccggcg cggacaccac ggacgcccgg gaccggctgg aggcgtacct cggcgacctg      660
atcgacgcca aggccaagga ggccgagccg ggcgacggca ttctggacga cctggtccac      720
aaccggctcc gcgcgggcga gctggaccgg agcgtcctgg tgtcgctcgc cgtcatcctg      780
ctggtcgccg ggcacgagac gaccgccaac atgatctccc tgggcaccta caccctgctc      840
cagcaccctg aacggctggc cgagctgcgc gccgaccgt cactgctgcc cgccgtcgtc      900
gaggaactgc tgcggatgct gtccatcgcc gagggcgtgc aacggctggc gctggaggac      960
atcgagatcg acggcatcac catccgggcc ggtgagggcg tcctcttctc cacctcggtc      1020
atcaaccggg acacggccgt ctacgaagac cccgacgacc tggacttcca ccgcgccgac      1080
cggcaccacg tggcgttcgg cttcggtatc caccagtgcc tgggccagaa cctggcccgc      1140
gcggaactgg agatcgccct cggtagcctg ttcacccggc tgcccgggct gcgtcttgcc      1200
gccccggccg aggagatccc cttcaaaccg ggcgacacgg tccaggggat gctggaactc      1260
cccgttacct ggtaagaggc ttcgctcatg cacatggaca tcgacatcga ccaggacgtc      1320
```

```
tgtatcggcg ccgggcagtg cgcgctggcg gcaccgggcg tcttcatcca ggacgacgac      1380
ggctacagca ccctgctgcc aggccaggag aacggcgtca ccgacccgat ggcccgggag      1440
gccgcccgcg cctgcccggt cagcgccatc accgtacggg agcgctccgc ctga           1494
```

<210> SEQ ID NO 2
<211> LENGTH: 1494
<212> TYPE: DNA
<213> ORGANISM: Artificial Sequence
<220> FEATURE:
<223> OTHER INFORMATION: Cloned version of SEQ ID NO: 1 with alternative
      stop codons

<400> SEQUENCE: 2

```
atgaagatcg gcacgacgca cctcactcgt ctgcgaggtc tttccatgac ggaactgacg       60
gacatcaccg gcccggctgc ccaggccgaa accgtcgcat tccccagga ccgcacctgt      120 ccctaccatc cccccaccgg atacgacccg ctgcgcgacg gcgaccccct gtcccgcgtc      180
accctctacg acggccgcga ggtctggctg gtcaccgccc aggccaccgc ccgcgccctg      240
ctcgccgacc cccggctgtc caccgaccgc cgccgcgacg gcttcccgt gccacccccc      300 cgcttcgcgg ccggccgcga ccgcacgctg ccctgctcg gctggacga ccccgaacac      360 caccggcagc gccggctgct catcccgtcg ttcaccctca aacgcgccac cgcacagcgc      420
ccctggatcc agcggatcgt cgacgaactg ctggacgcca tgatcgcccg ggggccggtc      480
gccgacctcg tgtccgcctt cgcgctgccc gtgccgtcca tggtcatctg cgaactgctc      540
ggcgtgccct acgccgacca cgagttcttc gaggaacagt cccgccggct gctgcgcggc      600
ccgaccggcg cggacaccac ggacgcccgg accggctgg aggcgtacct cggcgacctg      660
atcgacgcca aggccaagga ggccgagccg ggcgacggca ttctggacga cctggtccac      720
aaccggctcc gcgcgggcga gctggaccgg agcgtcctgg tgtcgctcgc cgtcatcctg      780
ctggtcgccg gcacgagac gaccgccaac atgatctccc tgggcaccta caccctgctc      840
cagcaccctg aacggctggc cgagctgcgc gccgacccgt cactgctgcc gccgtcgtc      900 gaggaactgc tgcggatgct gtccatcgcc gaggggctgc aacggctggc gctggaggac      960
atcgagatcg acggcatcac catccggggcc ggtgagggcg tcctcttctc cacctcggtc     1020
atcaaccggg acacgccgt ctacgaagac cccgacgacc tggacttcca ccgcgccgac      1080
cggcaccacg tggcgttcgg cttcggtatc caccagtgcc tgggccagaa cctggcccgc      1140
gcggaactgg agatcgccct cggtagcctg ttcacccggc tgcccgggct gcgtcttgcc      1200
gccccggccg aggagatccc cttcaaaccg ggcgacacgg tccaggggat gctggaactc      1260
cccgttacct ggtaagaggc ttcgctcatg cacatggaca tcgacatcga ccaggacgtc      1320
tgtatcggcg ccgggcagtg cgcgctggcg gcaccgggcg tcttcatcca ggacgacgac      1380
ggctacagca ccctgctgcc aggccaggag aacggcgtca ccgacccgat ggcccgggag      1440
gccgcccgcg cctgcccggt cagcgccatc accgtacggg agcgctccgc ctaa           1494
```

<210> SEQ ID NO 3
<211> LENGTH: 424
<212> TYPE: PRT
<213> ORGANISM: Streptomyces eurythermus

<400> SEQUENCE: 3

```
Met Lys Ile Gly Thr Thr His Leu Thr Arg Leu Arg Gly Leu Ser Met
1               5                   10                  15
```

-continued

```
Thr Glu Leu Thr Asp Ile Thr Gly Pro Ala Ala Gln Ala Glu Thr Val
             20                  25                  30
Ala Phe Pro Gln Asp Arg Thr Cys Pro Tyr His Pro Thr Gly Tyr
         35                  40                  45
Asp Pro Leu Arg Asp Gly Arg Pro Leu Ser Arg Val Thr Leu Tyr Asp
     50                  55                  60
Gly Arg Glu Val Trp Leu Val Thr Ala Gln Ala Thr Ala Arg Ala Leu
65                  70                  75                  80
Leu Ala Asp Pro Arg Leu Ser Thr Asp Arg Arg Asp Gly Phe Pro
                 85                  90                  95
Val Pro Thr Pro Arg Phe Ala Ala Gly Arg Asp Arg Thr Leu Ala Leu
                100                 105                 110
Leu Gly Leu Asp Asp Pro Glu His His Arg Gln Arg Leu Leu Ile
             115                 120                 125
Pro Ser Phe Thr Leu Lys Arg Ala Thr Ala Gln Arg Pro Trp Ile Gln
     130                 135                 140
Arg Ile Val Asp Glu Leu Leu Asp Ala Met Ile Ala Arg Gly Pro Val
145                 150                 155                 160
Ala Asp Leu Val Ser Ala Phe Ala Leu Pro Val Pro Ser Met Val Ile
                165                 170                 175
Cys Glu Leu Leu Gly Val Pro Tyr Ala Asp His Glu Phe Phe Glu Glu
             180                 185                 190
Gln Ser Arg Arg Leu Leu Arg Gly Pro Thr Gly Ala Asp Thr Thr Asp
         195                 200                 205
Ala Arg Asp Arg Leu Glu Ala Tyr Leu Gly Asp Leu Ile Asp Ala Lys
210                 215                 220
Ala Lys Glu Ala Glu Pro Gly Asp Gly Ile Leu Asp Asp Leu Val His
225                 230                 235                 240
Asn Arg Leu Arg Ala Gly Glu Leu Asp Arg Ser Val Leu Val Ser Leu
                245                 250                 255
Ala Val Ile Leu Leu Val Ala Gly His Glu Thr Thr Ala Asn Met Ile
             260                 265                 270
Ser Leu Gly Thr Tyr Thr Leu Leu Gln His Pro Glu Arg Leu Ala Glu
         275                 280                 285
Leu Arg Ala Asp Pro Ser Leu Leu Pro Ala Val Val Glu Glu Leu Leu
290                 295                 300
Arg Met Leu Ser Ile Ala Glu Gly Leu Gln Arg Leu Ala Leu Glu Asp
305                 310                 315                 320
Ile Glu Ile Asp Gly Ile Thr Ile Arg Ala Gly Glu Gly Val Leu Phe
                325                 330                 335
Ser Thr Ser Val Ile Asn Arg Asp Thr Ala Val Tyr Glu Asp Pro Asp
             340                 345                 350
Asp Leu Asp Phe His Arg Ala Asp Arg His His Val Ala Phe Gly Phe
         355                 360                 365
Gly Ile His Gln Cys Leu Gly Gln Asn Leu Ala Arg Ala Glu Leu Glu
370                 375                 380
Ile Ala Leu Gly Ser Leu Phe Thr Arg Leu Pro Gly Leu Arg Leu Ala
385                 390                 395                 400
Ala Pro Ala Glu Glu Ile Pro Phe Lys Pro Gly Asp Thr Val Gln Gly
                405                 410                 415
Met Leu Glu Leu Pro Val Thr Trp
             420
```

```
<210> SEQ ID NO 4
<211> LENGTH: 68
<212> TYPE: PRT
<213> ORGANISM: Streptomyces eurythermus

<400> SEQUENCE: 4

Met His Met Asp Ile Asp Ile Asp Gln Asp Val Cys Ile Gly Ala Gly
1               5                   10                  15

Gln Cys Ala Leu Ala Ala Pro Gly Val Phe Ile Gln Asp Asp Asp Gly
            20                  25                  30

Tyr Ser Thr Leu Leu Pro Gly Gln Glu Asn Gly Val Thr Asp Pro Met
        35                  40                  45

Ala Arg Glu Ala Ala Arg Ala Cys Pro Val Ser Ala Ile Thr Val Arg
    50                  55                  60

Glu Arg Ser Ala
65

<210> SEQ ID NO 5
<211> LENGTH: 56
<212> TYPE: DNA
<213> ORGANISM: Artificial Sequence
<220> FEATURE:
<223> OTHER INFORMATION: Primer Sequence

<400> SEQUENCE: 5
attttgttta actttaagaa ggagatatac atatgaagat cggcacgacg cacctc       56

<210> SEQ ID NO 6
<211> LENGTH: 60
<212> TYPE: DNA
<213> ORGANISM: Artificial Sequence
<220> FEATURE:
<223> OTHER INFORMATION: Primer Sequence

<400> SEQUENCE: 6
ctacccgcag agggcggggc ataagcttcc tattaggcgg agcgctcccg tacggtgatg   60

<210> SEQ ID NO 7
<211> LENGTH: 53
<212> TYPE: DNA
<213> ORGANISM: Artificial Sequence
<220> FEATURE:
<223> OTHER INFORMATION: Primer Sequence

<400> SEQUENCE: 7
gggtcctcaa cgacaggagc acgatcatgc cggaaataca ggaacgcacg ctg          53

<210> SEQ ID NO 8
<211> LENGTH: 56
<212> TYPE: DNA
<213> ORGANISM: Artificial Sequence
<220> FEATURE:
<223> OTHER INFORMATION: Primer Sequence

<400> SEQUENCE: 8
ttatcgccgg catggcggcc ccacgggtgc cggggcacaa ctcaatttgc gggtac       56

<210> SEQ ID NO 9
<211> LENGTH: 1275
<212> TYPE: DNA
<213> ORGANISM: Streptomyces eurythermus

<400> SEQUENCE: 9
atgaagatcg gcacgacgca cctcactcgt ctgcgaggtc tttccatgac ggaactgacg   60
```

```
gacatcaccg gcccggctgc ccaggccgaa accgtcgcat tcccccagga ccgcacctgt    120
ccctaccatc ccccaccgg atacgacccg ctgcgcgacg gcgacccct gtcccgcgtc      180 accctctacg acggccgcga ggtctggctg gtcaccgccc aggccaccgc ccgcgccctg    240
ctcgccgacc cccggctgtc caccgaccgc cgccgcgacg gcttcccgt gcccaccccc     300 cgcttcgcgg ccggccgcga ccgcacgctg gccctgctcg gctggacga ccccgaacac    360 caccggcagc gccggctgct catcccgtcg ttcaccctca aacgcgccac cgcacagcgc    420
ccctggatcc agcggatcgt cgacgaactg ctggacgcca tgatcgcccg ggggccggtc   480
gccgacctcg tgtccgcctt cgcgctgccc gtgccgtcca tggtcatctg cgaactgctc    540
ggcgtgccct acgccgacca cgagttcttc gaggaacagt cccgccggct gctgcgcggc   600
ccgaccggcg cggacaccac ggacgcccgg gaccggctgg aggcgtacct cggcgacctg    660
atcgacgcca aggccaagga ggccgagccg ggcgacggca ttctggacga cctggtccac   720
aaccggctcc gcgcgggcga gctggaccgg agcgtcctgg tgtcgctcgc cgtcatcctg    780
ctggtcgccg gcacgagac gaccgccaac atgatctccc tgggcaccta caccctgctc    840
cagcaccctg aacggctggc cgagctgcgc gccgacccgt cactgctgcc cgccgtcgtc    900
gaggaactgc tgcggatgct gtccatcgcc gaggggctgc aacggctggc gctggaggac    960
atcgagatcg acggcatcac catccggggcc ggtgagggcg tcctcttctc cacctcggtc   1020
atcaaccggg acacggccgt ctacgaagac cccgacgacc tggacttcca ccgcgccgac   1080
cggcaccacg tggcgttcgg cttcggtatc caccagtgcc tgggccagaa cctggcccgc   1140
gcggaactgg agatcgccct cggtagcctg ttcacccggc tgcccgggct gcgtcttgcc    1200
gccccggccg aggagatccc cttcaaaccg ggcgacacgg tccaggggat gctggaactc   1260
cccgttacct ggtaa                                                       1275

<210> SEQ ID NO 10
<211> LENGTH: 207
<212> TYPE: DNA
<213> ORGANISM: Streptomyces eurythermus

<400> SEQUENCE: 10
atgcacatgg acatcgacat cgaccaggac gtctgtatcg cgccgggca gtgcgcgctg        60 gcggcaccgg gcgtcttcat ccaggacgac gacggctaca gcaccctgct gccaggccag     120
gagaacggcg tcaccgaccc gatggcccgg gaggccgccc gcgcctgccc ggtcagcgcc     180
atcaccgtac gggagcgctc cgcctga                                         207

<210> SEQ ID NO 11
<211> LENGTH: 454
<212> TYPE: PRT
<213> ORGANISM: Streptomyces griseus

<400> SEQUENCE: 11

Met Pro Arg Pro Leu Arg Val Ala Ile Val Gly Ser Gly Pro Ala Gly
1               5                   10                  15

Ile Tyr Ala Ala Asp Ala Leu Leu Lys Ser Glu Val Ala Ala Asp Pro
            20                  25                  30

Gly Val Ser Ile Asp Ile Phe Glu Arg Met Pro Ala Pro Phe Gly Leu
        35                  40                  45

Ile Arg Tyr Gly Val Ala Pro Asp His Pro Arg Ile Lys Gly Ile Ile
    50                  55                  60
```

```
Thr Ala Leu His Gln Val Leu Asp Lys Pro Gln Ile Arg Leu Phe Gly
 65                  70                  75                  80

Asn Val Asn Tyr Pro Thr Asp Val Ser Leu Asp Asp Leu Arg Ala Phe
                 85                  90                  95

Tyr Asp Gly Val Ile Phe Ala Thr Gly Ala Thr Ala Asp Arg Asp Leu
            100                 105                 110

Ser Leu Pro Gly Ile Asp Leu Asp Gly Ser Tyr Gly Ala Ala Asp Phe
        115                 120                 125

Val Ala Trp Tyr Asp Gly His Pro Asp Phe Pro Arg Thr Trp Pro Leu
    130                 135                 140

Glu Ala Glu Lys Val Ala Val Leu Gly Val Gly Asn Val Ala Leu Asp
145                 150                 155                 160

Ile Ala Arg Val Leu Ala Lys Thr Ala Asp Glu Leu Leu Pro Thr Glu
                165                 170                 175

Ile Pro Pro Asn Val Tyr Glu Gly Leu Lys Ala Asn Lys Ala Leu Glu
            180                 185                 190

Val His Val Phe Gly Arg Arg Gly Pro Ala Gln Ala Lys Phe Ser Pro
        195                 200                 205

Met Glu Leu Arg Glu Leu Asp His Ser Pro Asn Ile Glu Val Ile Val
    210                 215                 220

Asp Pro Glu Asp Ile Asp Tyr Asp Glu Gly Ser Ile Ala Thr Arg Arg
225                 230                 235                 240

Gly Asn Lys Gln Ala Asp Met Val Ala Lys Thr Leu Glu Asn Trp Ala
                245                 250                 255

Ile Arg Asp Val Gly Asp Arg Pro His Lys Leu Phe Leu His Phe Phe
            260                 265                 270

Glu Ser Pro Ala Glu Ile Leu Gly Glu Asp Gly Arg Val Thr Gly Leu
        275                 280                 285

Arg Thr Glu Arg Thr Glu Leu Asp Gly Thr Gly Asn Val Lys Gly Thr
    290                 295                 300

Gly Glu Phe Lys Asp Trp Asp Val Gln Ala Val Tyr Arg Ala Val Gly
305                 310                 315                 320

Tyr Leu Ser Asp Gln Leu Pro Lys Leu Pro Trp Asp Leu Glu Thr Gly
                325                 330                 335

Thr Val Pro Asp Ala Gly Gly Arg Val Val Gln Glu Ser Gly Glu His
            340                 345                 350

Leu Gln Ser Thr Tyr Val Thr Gly Trp Ile Arg Arg Gly Pro Ile Gly
        355                 360                 365

Leu Ile Gly His Thr Lys Gly Asp Ala Asn Glu Thr Val Ser Asn Leu
    370                 375                 380

Leu Asp Asp Tyr Ala Asn Gly Arg Leu Gln Thr Pro Ser Ser Pro Ala
385                 390                 395                 400

Pro Glu Ala Val Asp Ala Phe Leu Ala Glu Arg Asn Val Arg Phe Thr
                405                 410                 415

Thr Trp Asp Gly Trp Tyr Arg Leu Asp Ala Ala Glu Lys Ala Gln Gly
            420                 425                 430

Glu Pro His Gly Arg Glu Arg Val Lys Tyr Val Glu Arg Glu Asp Met
        435                 440                 445

Leu Arg Glu Ser Gly Ala
    450

<210> SEQ ID NO 12
<211> LENGTH: 1365
<212> TYPE: DNA
```

<213> ORGANISM: Streptomyces griseus

<400> SEQUENCE: 12

```
atgccccgcc ctctgcgggt agccatcgtc ggatccggcc cggccgggat ctacgccgcc      60
gacgccctgc tcaagtccga agtggccgcc gaccccggtg tttccatcga catcttcgag     120
cgcatgcccg ccccgttcgg cctcatccgg tacgcgtcg cgcccgacca cccgcggatc     180
aagggcatca tcacggccct ccaccaggtg ctcgacaagc gcagatccg cctcttcggc     240
aacgtgaact accccaccga cgtcagcctg gacgatctgc gcgccttcta cgacggtgtg     300
atcttcgcca ccggcgccac ggcggaccgg gacctgtccc tcccgggcat cgacctcgac     360
ggctcgtacg gcgcggccga cttcgtcgcc tggtacgacg gccaccccga cttcccgcgc     420
acctggccgc tggaggcgga gaaagtcgcc gtcctcggtg tcggcaacgt cgccctggac     480
atcgcgcgcg tcctcgccaa gacggccgac gagctgctgc gaccgagat cccgccgaac     540
gtctacgagg cctcaaggc caacaaggcg ctggaggtgc acgtcttcgg ccgccgcggc     600
ccggcgcagg cgaagttcag cccgatggag ctgcgggagc tggaccactc ccccaacatc     660
gaggtgatcg tcgaccccga ggacatcgac tacgacgagg gctcgatcgc gacccggcgc     720
ggcaacaagc aggccgacat ggtcgccaag accctggaga actgggcgat ccgcgacgtc     780
ggcgaccggc cgcacaagct gttcctgcac ttcttcgagt cgcccgcgga gatcctcggc     840
gaggacggca gggtgaccgg cctgcgcacc gagcgcacgg agctggacgg cacgggcaac     900
gtcaagggca ccggcgagtt caaggactgg gacgtccagg cggtctaccg ggccgtcggc     960
tacctctccg accagctgcc caagctgccc tgggacctcg agacgggcac ggtcccggac    1020
gcgggcggcc gggtcgtcca ggagtccggc gagcacctcc agtcgacgta cgtcaccggc    1080
tggatccggc gcggtccgat cggcctgatc ggccacacca agggcgacgc caacgagacg    1140
gtgtccaacc tgctggacga ctacgcgaac ggccgtctcc agacgccctc ctcccccgct    1200
cccgaggccg tggacgcgtt cctcgccgag cggaacgtcc gcttcaccac ctgggacggc    1260
tggtaccggc tcgacgccgc ggagaaggcg cagggcgaac cgcacgggcg tgagcgcgtg    1320
aagtacgtcg agcgcgagga catgctccgc gagagcggcg cctaa                    1365
```

<210> SEQ ID NO 13
<211> LENGTH: 404
<212> TYPE: PRT
<213> ORGANISM: Amycolatopsis lurida

<400> SEQUENCE: 13

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110
```

```
Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
        130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Thr Ala Thr Ser Arg Phe Ala Thr Ala Asp Val Glu Ile Gly
        290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 14
<211> LENGTH: 395
<212> TYPE: PRT
<213> ORGANISM: Streptomyces rimosus

<400> SEQUENCE: 14

Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Arg Gln
    50                  55                  60

Asn Pro Ala Phe Pro Ser Pro Ala Pro Arg Phe Glu Thr Leu Arg Lys
65                  70                  75                  80
```

```
Val Arg Thr Pro Leu Leu Gly Val Asp Asp Pro Glu His Asn Thr Gln
            85                  90                  95

Arg Arg Met Leu Ile Pro Ser Phe Ser Val Lys Arg Ala Ala Ala Leu
        100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
        130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Leu Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
        210                 215                 220

Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
        290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
        370                 375                 380

Leu Gln Gly Leu Val Glu Leu Pro Val Thr Trp
385                 390                 395

<210> SEQ ID NO 15
<211> LENGTH: 403
<212> TYPE: PRT
<213> ORGANISM: Streptomyces rimosus

<400> SEQUENCE: 15

Met Pro Glu Ile Ile Asp Leu Gly Ala Tyr Gly Pro Asp Phe Val Ala
1               5                   10                  15

Asp Pro His Pro Tyr Tyr Ala Lys Leu Arg Ala Gln Gly Pro Val His
            20                  25                  30

Arg Val Arg Ala Pro Glu Met Glu Pro Glu Phe Pro Gln Ala Trp Leu
        35                  40                  45

Ile Val Gly Tyr Asp Glu Ala Arg Ala Val Leu Ala Asp Asn Arg Phe
    50                  55                  60
```

```
Ala Lys Asp Trp Ser Arg Ala Asn Gly Ser Leu Ala Asp Ser Glu Val
 65                  70                  75                  80

Leu Ala Glu Trp Gln Leu Met Asn Met Leu Asp Ala Asp Pro Pro Gln
                 85                  90                  95

His Thr Arg Leu Arg Lys Leu Val Ala Arg Glu Phe Thr Thr Arg Arg
            100                 105                 110

Val Glu Ala Leu Arg Pro Arg Val Gln Gln Ile Thr Asp Glu Leu Leu
            115                 120                 125

Asp Ala Met Leu Ala Ala Pro Asp Gly Arg Ala Asp Leu Val Glu Ala
            130                 135                 140

Leu Ala Phe Pro Leu Pro Met Thr Val Ile Cys Glu Leu Leu Gly Val
145                 150                 155                 160

Pro Asp Ile Glu Arg Asp Thr Phe Arg Ala Trp Ser Asn Glu Leu Val
                165                 170                 175

Ser Pro Thr Asp Asn Glu Ala Thr Met Thr Ala Ala Arg Glu Met Ala
            180                 185                 190

Ala Tyr Leu Asp Gly Leu Ile Glu Ser Lys Arg Ser Ser Pro Gly Glu
            195                 200                 205

Asp Leu Leu Ser Ala Leu Val Arg Thr Ser Asp Glu Asp Gly Asp Gln
210                 215                 220

Leu Ser Arg Gln Glu Leu Leu Gly Met Ala Phe Leu Leu Leu Val Ala
225                 230                 235                 240

Gly His Glu Thr Thr Val Asn Leu Ile Ser Asn Gly Val Arg Ala Leu
                245                 250                 255

Leu Gln His Pro Ala Gln Leu Ala Ala Leu Arg Ala Asp Pro Ser Leu
            260                 265                 270

Leu Asp Asn Ala Val Glu Glu Met Leu Arg Tyr Asp Gly Pro Val Glu
            275                 280                 285

Thr Ala Thr Trp Arg Phe Thr Ala Glu Pro Val Gly Ile Gly Gly Val
            290                 295                 300

Glu Ile Pro Ala Gly Glu Ile Val Leu Val Gly Leu Ala Gly Ala Asp
305                 310                 315                 320

Arg Asp Pro Glu Arg Phe Glu Ala Pro Asp Thr Phe Asp Ile Thr Arg
                325                 330                 335

Glu Thr Arg Gly His Val Ala Phe Gly His Gly Ile His Phe Cys Leu
            340                 345                 350

Gly Ala Pro Leu Ala Arg Val Glu Gly Arg Ile Ala Val Arg Thr Leu
            355                 360                 365

Leu Asp Arg Cys Pro Asp Leu Ala Leu Asp Thr Ala Pro Glu Ala Leu
            370                 375                 380

Thr Trp Arg Ala Gly Met Thr Ile Arg Gly Pro Gln His Leu Pro Val
385                 390                 395                 400

Arg Trp Arg

<210> SEQ ID NO 16
<211> LENGTH: 454
<212> TYPE: PRT
<213> ORGANISM: Streptomyces rimosus

<400> SEQUENCE: 16

Met Thr Thr Ser Pro Thr Glu Ser Thr Thr Ala Thr Pro Pro Asp Ser
1               5                  10                  15

Thr Thr Ala Ser Ala Pro Gly Thr Pro Pro Asp Ala Leu Pro Ser Tyr
            20                  25                  30
```

```
Val Gly Leu His Pro Gly Pro Asn Val Met Glu Pro Glu Leu Leu
         35                  40                  45
Asn Asp Pro Tyr Ala Gly Tyr Gly Lys Leu Arg Glu Gln Gly Ala Leu
     50                  55                  60
Val Arg Gly Arg Phe Leu Asp Asp Ser Pro Val Trp Leu Val Thr Arg
 65                  70                  75                  80
Phe Asp Val Val Arg Glu Val Met Arg Asp Pro Arg Phe Ile Asn Asn
                 85                  90                  95
Pro Ser Arg Leu Pro Gly Arg Thr Glu Lys Asp Pro Arg Ala Gln Leu
            100                 105                 110
Ile Glu Leu Phe Gly Ile Pro Asp His Met Ala Arg Tyr Leu Val Asp
            115                 120                 125
Thr Ile Leu Thr Ser Asp Pro Asp His Thr Arg Leu Arg Arg Leu
            130                 135                 140
Val Ser Arg Ala Phe Thr Ala Arg Arg Ile Gln Asp Leu Arg Pro Arg
145                 150                 155                 160
Val Glu Ala Ile Thr Asp Glu Leu Leu Asp Arg Leu Pro Ala His Ala
                 165                 170                 175
Gln Asp Gly Val Val Asp Leu Val Glu His Phe Ala Tyr Pro Leu Pro
            180                 185                 190
Ile Thr Val Ile Cys Glu Leu Val Gly Ile Asp Glu Glu Asp Arg Pro
            195                 200                 205
Leu Trp Arg Gln Phe Gly Ala Asp Leu Thr Ser Leu Glu Pro Lys Arg
     210                 215                 220
Ile Gly Ala Thr Val Pro Ala Met Val Glu His Ile His Lys Val Ile
225                 230                 235                 240
Gly Glu Arg Gln Ser Ala Leu Arg Asp Asp Leu Leu Ser Ala Leu Ile
                 245                 250                 255
Arg Ala Arg Asp Asp Asp Gly Gly Arg Leu Ser Glu Thr Glu Met Val
            260                 265                 270
Thr Met Val Leu Thr Leu Val Leu Ala Gly His Glu Thr Thr Ala His
     275                 280                 285
Leu Ile Ser Asn Gly Thr Leu Ala Leu Leu Thr His Pro Asp Gln Arg
     290                 295                 300
Arg Leu Leu Thr Glu Asp Pro Gly Leu Leu Pro Arg Ala Val His Glu
305                 310                 315                 320
Leu Met Arg Trp Cys Gly Pro Ile Gln Ala Thr Gln Leu Arg Tyr Ala
                 325                 330                 335
Ser Glu Asp Val Glu Val Ala Gly Thr Gln Val His Lys Gly Asp Ala
            340                 345                 350
Leu Met Phe Ser Leu Val Ala Ala Asn His Asp Pro Arg His Tyr Thr
            355                 360                 365
Glu Pro Glu Lys Leu Asp Leu Thr Arg Gln Pro Ala Gly Arg Ala Glu
     370                 375                 380
Asp His Val Gly Phe Gly His Gly Met His Tyr Cys Leu Gly Ala Ser
385                 390                 395                 400
Leu Ala Arg Gln Glu Gly Glu Val Ala Phe Gly Lys Leu Leu Ala Arg
                 405                 410                 415
Tyr Pro Glu Val Ala Leu Ala Leu Pro His Glu Gln Leu Glu Glu Gln
            420                 425                 430
Glu Arg Ile Arg Gln Pro Gly Ser Trp Arg Leu Arg Arg Leu Pro Leu
            435                 440                 445
```

Arg Leu Arg Pro Glu Asp
            450

<210> SEQ ID NO 17
<211> LENGTH: 399
<212> TYPE: PRT
<213> ORGANISM: Streptomyces platensis

<400> SEQUENCE: 17

Met Ala Glu Ile Val Asp Leu Gly Ala Tyr Gly Lys Asp Phe Thr Arg
1               5                   10                  15

Asp Pro Tyr Pro Tyr Tyr Ala Lys Leu Arg Ala Gln Gly Pro Ile His
            20                  25                  30

Arg Val Arg Leu Pro Tyr Gly Asn Asp Val Trp Leu Val Val Gly His
        35                  40                  45

Gln Ala Val Arg Ala Ala Leu Ser Asp Ser Arg Leu Asn Lys Asp Trp
    50                  55                  60

Arg Ala Ala Met Pro Gln Gly Asp Val Gly Glu Glu Ser Ala Leu Phe
65                  70                  75                  80

Thr Asn Met Leu Asp Ala Asp Pro Pro Gln His Thr Arg Leu Arg Lys
                85                  90                  95

Leu Val Ala Lys Glu Phe Thr Ser Arg Arg Val Glu Ala Leu Arg Pro
            100                 105                 110

Arg Val Gln Gln Ile Thr Asp Glu Leu Leu Asp Thr Met Leu Ala Ala
        115                 120                 125

Pro Asp Gly Arg Ala Asp Leu Val Glu Ala Leu Ala Phe Pro Leu Pro
    130                 135                 140

Met Thr Val Ile Cys Glu Leu Leu Gly Val Pro Ser Met Asp Arg Asp
145                 150                 155                 160

Ala Phe Arg Ser Trp Ser Asn Glu Ile Val Ala Pro Thr Ser Asp Glu
                165                 170                 175

Ala Ala Gln Ala Ala Val Val Ala Met Ser Gly Tyr Leu Val Glu Leu
            180                 185                 190

Ile Glu Thr Lys Arg Asn Ala Pro Gly Asp Gly Leu Leu Ser Ala Leu
        195                 200                 205

Ile Arg Thr Ser Asp Glu Asp Gly Asp Gln Leu Ser Arg Asp Glu Leu
    210                 215                 220

Val Gly Thr Ala Phe Leu Leu Val Ala Gly His Glu Thr Thr Val
225                 230                 235                 240

Ser Leu Leu Ala Asn Gly Val Arg Ala Leu Leu Gln His Pro Asp Gln
                245                 250                 255

Leu Ala Ala Leu Arg Ala Asp Phe Ser Leu Leu Asp Asn Ala Val Glu
            260                 265                 270

Glu Met Leu Arg Tyr Asp Gly Pro Val Glu Thr Ala Thr Trp Arg Phe
        275                 280                 285

Thr Gly Glu Pro Val Glu Ile Gly Gly Thr Leu Ile Pro Ala Gly Glu
    290                 295                 300

Thr Val Ala Ile Ala Leu Ala Ser Ala Ser Arg Asp Pro Glu Ile Phe
305                 310                 315                 320

Ala Val Ala Asp Asp Phe Asp Ile Thr Arg Asp Ala Arg Gly His Thr
                325                 330                 335

Ala Phe Gly His Gly Ile His Phe Cys Leu Gly Ala Pro Leu Ala Arg
            340                 345                 350

Leu Glu Ala Arg Ile Ala Leu Arg Ser Leu Leu Glu Arg Cys Pro Asp
        355                 360                 365

```
Leu Ala Met Asp Ala Asp Phe Asp Asp Leu Thr Trp Arg Val Gly Met
    370                 375                 380

Leu Arg Gly Pro Ala Arg Leu Pro Val Arg Trp Lys Ser Trp Ser
385                 390                 395
```

BIOCATALYTIC TECHNIQUES

FIELD OF THE INVENTION

The present invention relates to a cytochrome P450 enzyme from *Streptomyces eurythermus* NRRL 2539, nucleic acids encoding the enzyme, kits comprising the enzyme, and uses of the enzyme for catalysing the oxidation of organic substrates.

BACKGROUND OF INVENTION

Cytochrome P450 (CYP) is a superfamily of haem-thiolate proteins named for the spectral absorbance peak of their carbon-monoxide bound species at 450 nm. They are found in all kingdoms of life such as animals, plants, fungi, protists, bacteria, archaea, and furthermore a putative P450 from giant virus *Acanthamoeba polyphaga* has been proposed, Lamb, D C; Lei, L; Warrilow, A G; Lepesheva, G I; Mullins, J G; Waterman, M R; Kelly, S L (2009). "*The first virally encoded cytochrome P450*". Journal of Virology. 83 (16): pp8266-9. Cytochrome P450 enzymes have not been identified in *E. coli*, Roland Sigel; Sigel, Astrid; Sigel, Helmut (2007). The Ubiquitous Roles of Cytochrome P450 Proteins: Metal Ions in Life Sciences. New York: Wiley. ISBN 0-470-01672-8; Danielson P B (December 2002). "The cytochrome P450 superfamily: biochemistry, evolution and drug metabolism in humans". Curr. Drug Metab. 3 (6): pp561-97.

Cytochrome P450s show extraordinary diversity in their reaction chemistry supporting the oxidative, peroxidative and reductive metabolism of a diverse range of endogenous and xenobiotic substrates.

In humans, cytochrome P450s are best known for their central role in phase I drug metabolism where they are of critical importance for two of the most significant problems in clinical pharmacology: drug-drug interactions and inter-individual variability in drug metabolism.

The most common reaction catalyzed by cytochromes P450 is a mono-oxygenase reaction. Cytochrome P450 mono-oxygenases use a haem group to oxidise molecules, often making them more water-soluble by either adding or unmasking a polar group. In general the reactions catalysed by these enzymes can be summarised as:

In the first line example, R—H is the substrate and R—OH is the oxygenated substrate. The oxygen is bound to the haem group in the core of the CYP enzyme, protons (H+) are usually indirectly derived from the reduced cofactor NADH or NADPH via redox partner proteins, either discrete proteins or fused to the CYP, through specific amino acids in the CYP enzyme. CYP enzymes can receive electrons from a range of redox partner proteins such as cytochrome b5, a ferredoxin reductase and a ferredoxin, and adrenodoxin reductase and adrenodoxin.

Although classification and nomenclature of cytochrome P450 is quite complex, they can be classified by their redox partner transfer protein system, proposed by I. Hanukoglu (1996). "*Electron Transfer Proteins of Cytochrome P450 Systems*". Advances in Molecular and Cell Biology. Advances in Molecular and Cell Biology. 14: 29-56. In summary, cytochrome P450 enzymes can be classified into the following groups:

Microsomal P450 systems which utilise cytochrome P450 reductase or cytochrome b5 to transfer electrons from cofactor to cytochrome P450;

Mitochondrial P450 systems which utilise adrenodoxin reductase and adrenodoxin to transfer electrons from reduced cofactor to cytochrome P450;

Bacterial P450 systems which utilise ferredoxin reductase and ferredoxin proteins to transfer electrons from reduced cofactor to cytochrome P450;

CYB5R-cytb5-P450 systems, which utilise cytochrome b5 for the electron transfer from the cofactor to the cytochrome P450;

FMN-Fd-P450 systems in which the electron partner reductase is a fused FMN domain;

P450 only systems that do not require redox partner proteins, e.g., $P450_{BM-3}$.

Isolated bacterial cytochrome P450 enzymes are known, including $P450_{cam}$ from *Pseudomonas putida*, J Biol Chem (1974) 249, 94; $P450_{BM-1}$ and $P450_{B-3}$ both from *Bacillus megaterium* ATCC 14581, Biochim Biophys Acta (1985) 838, 302, and J Biol Chem (1986) 261, 1986, 7160; P450a, P450b, and P450c from *Rhizobium japonicum*, Biochim Biophys Acta (1967) 147, 399; and P450npd from *Nocardia* NHI, Microbios (1974) 9, 119.

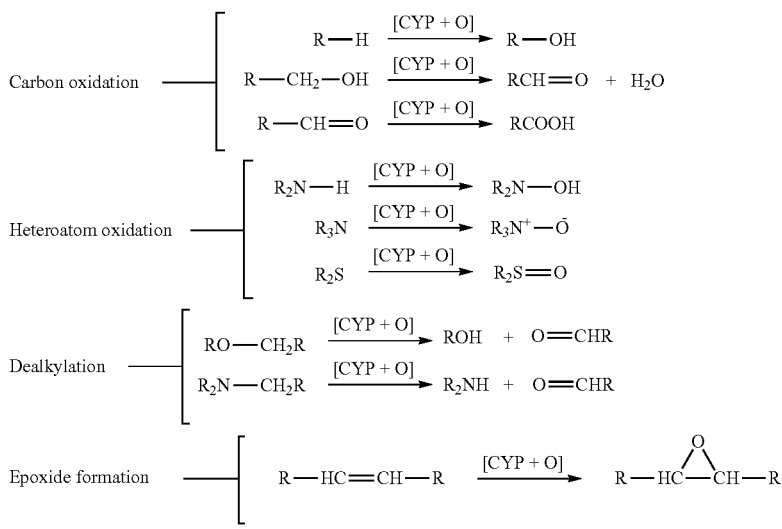

However, cytochrome P450 enzymes purified from Actinomycete microorganisms remain relatively unreported. The induction of a cytochrome P450 in *Streptomyces griseus* by soybean flour (P450$_{soy}$) is described in Biochem and Biophys Res Comm (1986) 141, 405. Other reported examples include the isolation and properties of two forms of a P450 effecting pesticide inactivation (P450$_{SU1}$ & $_{SU2}$) and two forms of 6-deoxyerythronolide B hydroxylase from *Saccharopolyspora erythraea* (originally classified as *Streptomyces erythraeus*) as described in Biochemistry (1987) 26, 6204. U.S. Pat. No. 6,884,608 describes enzymatic hydroxylation of epothilone B to epothilone F, effected with a hydroxylation enzyme produced by a strain of *Amycolatopsis orientalis* (originally classified as *Streptomyces orientalis*). A more recent example is CYP107L from *Streptomyces platensis* DSM40041, reported in Biotechnology and Bioengineering (2018) 115; 2156-2166 for exhibiting activities resembling some human drug metabolising P450 enzymes.

In the field of medicinal chemistry, modifications to chemical compounds are used to alter the properties of such chemical compounds. For example, tertiary butyl moieties are often used by medicinal chemists in the synthesis of drug-like molecules for introduction of hydrophobicity. However, further modifications thereof can be used to improve potency, selectivity and solubility profiles of such compounds, for example hydroxylations can be used. Hydroxylations are also the main route of metabolic degradation, another important aspect of pharmacology and medicinal chemistry. Methods for the production of these hydroxylated metabolites are sought using biotransformation with animal tissues due to being often challenging to synthesise by purely chemical means.

SUMMARY OF THE INVENTION

It has surprisingly been found that a specific cytochrome P450 enzyme found in *Streptomyces eurythermus* NRRL 2539 can be used for providing different types of oxidation reactions upon a range of organic substrates, the term oxidation and terms derived thereof referring to reaction types including but not limited to hydroxylation, epoxidation, carboxylation and dealkylation of the substrates.

In particular, cytochrome P450 enzyme having the amino acid sequence shown as SEQ ID NO: 3 can be used for the oxidation of organic compounds in order to activate or modify a compound's physicochemical and pharmacological properties. In a particularly preferred embodiment, the cytochrome P450 enzyme having the amino acid sequence shown as SEQ ID NO: 3 is useful for the oxidation of a variety of aliphatic and aromatic moieties, or chemicals containing such moieties, for the purposes of C—H activation or modification of a compound's physicochemical and pharmacological properties. The cytochrome P450 enzyme of SEQ ID NO: 3 has not previously been identified and due to its wide reactivity and superior activity on a number of substrates is a particularly useful cytochrome P450 for industrial use.

In a first aspect, the invention provides a cytochrome P450 enzyme comprising the amino acid sequence set forth in SEQ ID NO: 3, or a variant thereof having an amino acid sequence having at least 95% identity thereto and having CYP450 activity.

In a second aspect, the invention provides a nucleic acid molecule comprising a nucleotide sequence encoding an enzyme of the invention.

In a third aspect, the invention provides a recombinant construct comprising a nucleic acid molecule of the invention operatively linked to a heterologous expression control sequence.

In a fourth aspect, the invention provides a vector comprising the nucleic acid molecule or recombinant construct of the invention.

In a fifth aspect, the invention provides a microorganism comprising the nucleic acid molecule, the recombinant construct or the vector of the invention, wherein the nucleotide sequence encoding the enzyme of the invention is heterologous to the microorganism, wherein preferably the microorganism is not Streptomyces eurythermus.

In a sixth aspect, the invention provides the use of a cytochrome P450 enzyme comprising SEQ ID NO: 3 or a variant thereof having at least 95% identity thereto and having CYP450 activity, for the oxidation of an organic compound.

In a seventh aspect, the invention provides a method for the production of an oxidised organic compound, comprising reacting the organic compound with a cytochrome P450 enzyme comprising SEQ ID NO: 3 or a variant thereof having at least 95% identity thereto and having CYP450 activity.

In an eighth aspect, the invention provides a kit comprising:
  i) a cytochrome P450 enzyme comprising SEQ ID NO: 3 or a variant thereof having at least 95% identity thereto and having CYP450 activity;
  ii) a microorganism that expresses a cytochrome P450 enzyme comprising SEQ ID NO: 3 or a variant thereof having at least 95% identity thereto and having CYP450 activity, or a lysate of said microorganism; and/or
  iii) a nucleic acid molecule, recombinant construct or vector of the invention;
  optionally wherein the kit further comprises instructions and other cofactor reagents for use for the oxidation of an organic compound.

In a ninth aspect, the invention provides a method of producing a cytochrome P450 enzyme of the invention, the method comprising introducing a nucleic acid molecule, a recombinant construct or a vector of the invention, into a microorganism, and expressing the cytochrome P450 enzyme in the microorganism, and optionally isolating and/or purifying the cytochrome P450 enzyme.

BRIEF DESCRIPTION OF THE FIGURES

The invention is described with reference to the accompanying drawings, wherein:

FIG. 1(*a*) shows epoxidation of carbamazepine, FIG. 1(*b*) shows hydroxylation of bosentan (with demethylation as a minor side reaction), FIG. 1(*c*) shows hydroxylation of diclofenac, FIG. 1(*d*) shows hydroxylation of a methyl group of meloxicam, with some further oxidation to yield a carboxyl moiety, FIG. 1(*e*) shows hydroxylation of tivantinib, and FIG. 1(*f*) shows hydroxylation of ambroxide;

Figure 1:
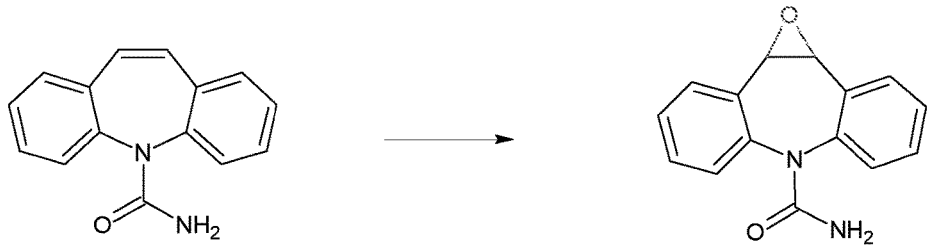
FIG. 1 shows schematic examples of biotransformations effected by the use of the cytochrome P450 enzyme comprising SEQ ID NO: 3 of the present invention.
Figure 1:
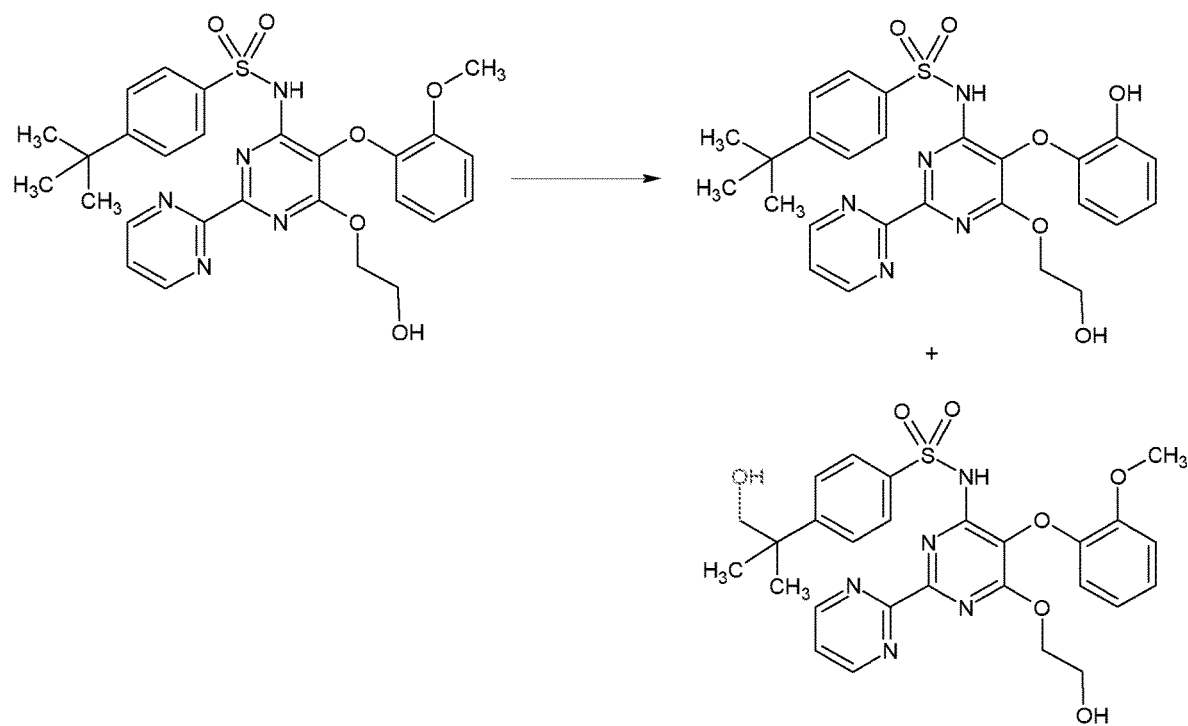
Figure 1:
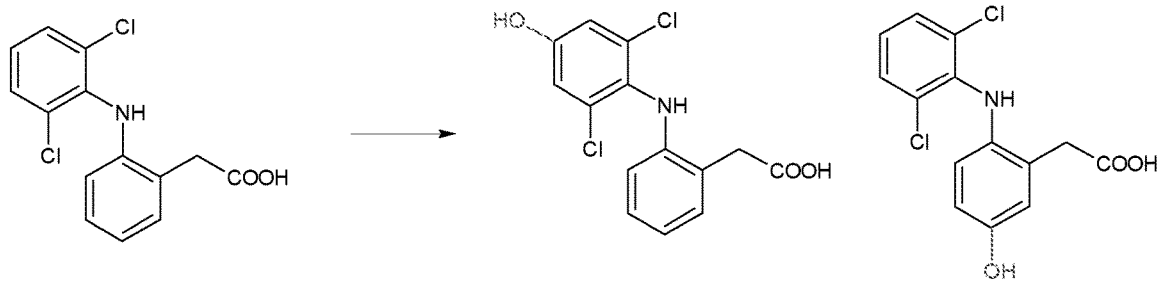
Figure 1:
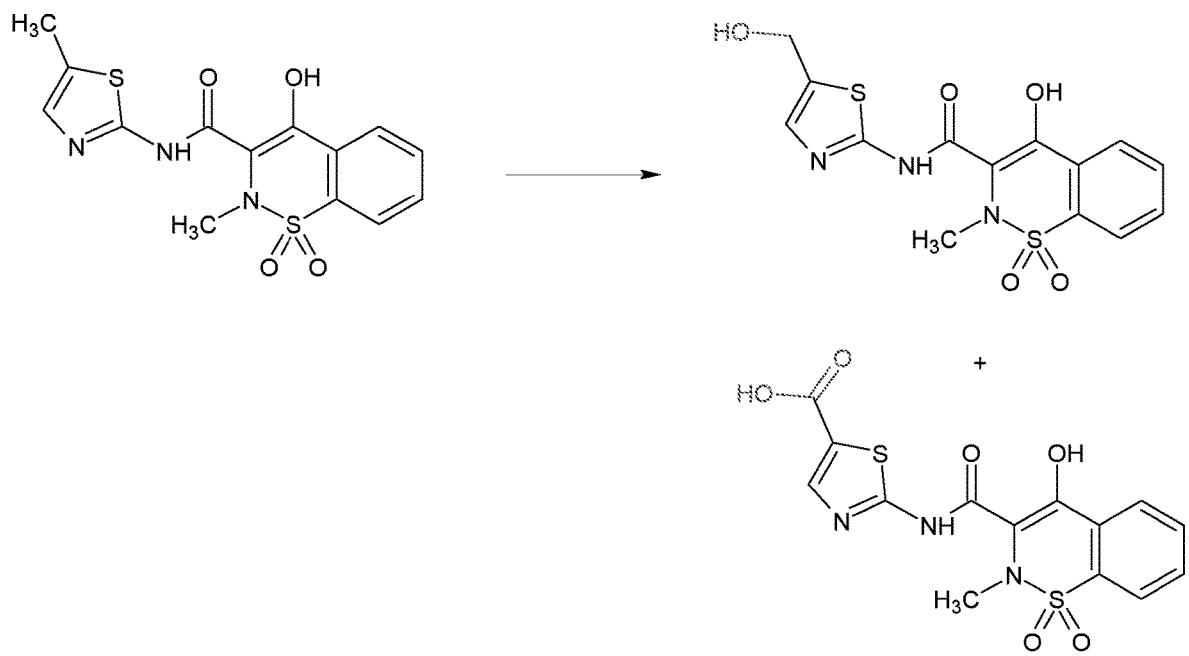
Figure 1:
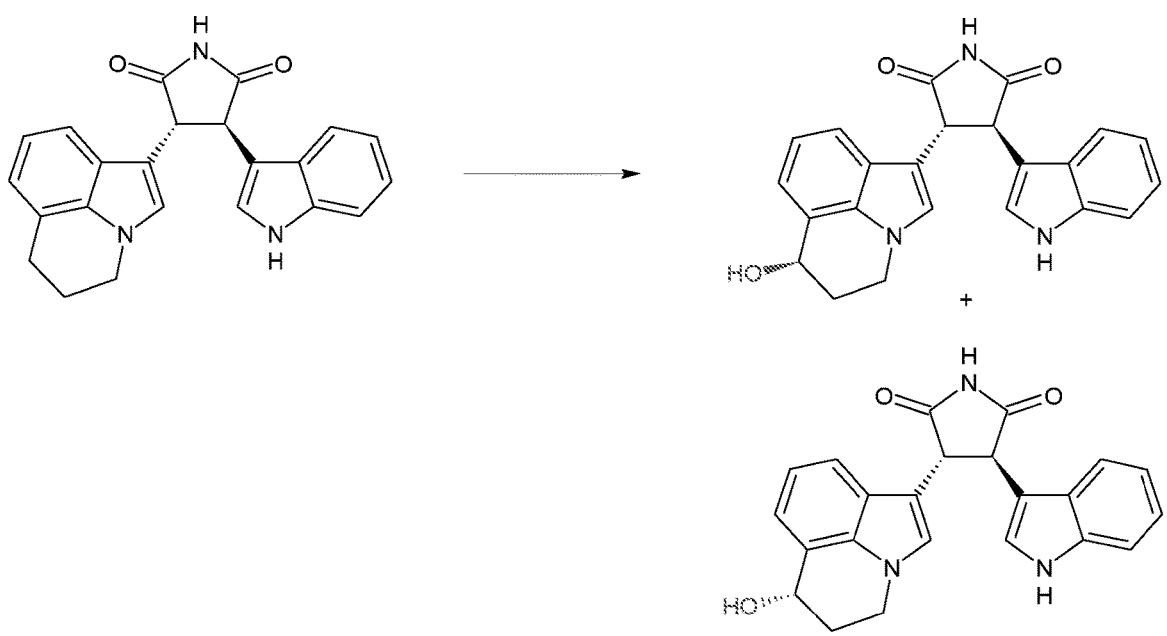
Figure 1:
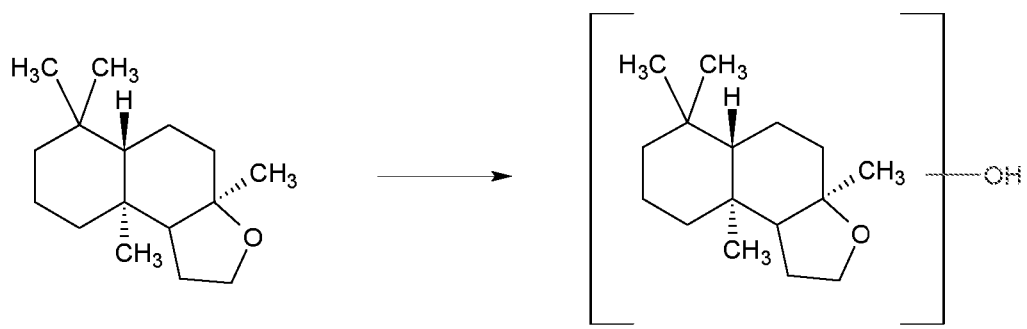

4a shows chromatograms of post-reaction extract using lyophilised material of recombinant P450$_{SeuC10}$, ferredoxin$_{seuF08}$ and ferredoxin reductase$_{SCF15A}$, as described in Example 4A, dosed with 100 mg/L carbamazepine. Top to bottom is UV$_{225\ nm}$, EIC$_{237\ m/z}$ (carbamazepine, 1.33 mins) and EIC$_{253\ m/z}$ (carbamazepine-10,11-epoxide, 1.16 mins (49% inferred yield));

4b shows chromatograms of post-reaction extract using *E. coli* expressing recombinant P450$_{SeuC10}$, ferredoxin$_{seuF08}$ and ferredoxin reductase$_{SCF15A}$, as described in Example 4B, dosed with 100 mg/L bosentan. Top to bottom is UV$_{268\ nm}$, EIC$_{552\ m/z}$ (bosentan, 1.76 mins)), EIC$_{538\ m/z}$ (O-desmethylbosentan, 1.67 minute (3.4% inferred yield)) and EIC$_{568\ m/z}$ (hydroxy-bosentan, 1.44 mins (81% inferred yield));

4c shows chromatograms of post-reaction extract using *E. coli* expressing recombinant P450$_{SeuC10}$, ferredoxin$_{seuF08}$ and ferredoxin reductase$_{SCF15A}$, as described in Example 4B, dosed with 100 mg/L diclofenac. Top to bottom is UV$_{275\ nm}$, EIC$_{294\ m/z}$ (diclofenac, 1.83 mins)), EIC$_{310\ m/z}$ (5-hydroxydiclofenac and 4'-hydroxydiclofenac, 1.59 minutes (19.4% inferred yield) and 1.64 minutes (73.4% inferred yield), respectively);

4d shows chromatograms of post-reaction extract using lyophilised material of recombinant P450$_{SeuC10}$, ferredoxin$_{seuF08}$ and ferredoxin reductase$_{SCF15A}$, as described in Example 4A, dosed with 100 mg/L meloxicam. Top to bottom is UV$_{354\ nm}$, EIC$_{352\ m/z}$ (meloxicam, 1.61 mins), EIC$_{368\ m/z}$ (5'-hydroxymethylmeloxicam, 1.32 mins (28.4% inferred yield) and EIC$_{382\ m/z}$ (5'-carboxylmeloxicam, 1.54 mins (5.3% inferred yield));

4e shows chromatograms of post-reaction extract using lyophilised material of recombinant P450$_{SeuC10}$, ferredoxin$_{seuF08}$ and ferredoxin reductase$_{SCF15A}$, as described in Example 4A, dosed with 100 mg/L tivantinib. Top to bottom is UV$_{280\ nm}$, EIC$_{370\ m/z}$ (tivantinib, 1.55 mins) and EIC$_{386\ m/z}$ (epimeric benzylic hydroxylation products of tivantinib, 1.16 and 1.14 mins (98.3% combined inferred yield));

4f shows chromatograms of post-reaction extract using lyophilised material of recombinant P450$_{SeuC10}$, ferredoxin$_{seuF08}$ and ferredoxin reductase$_{SCF15A}$, as described in Example 4A, dosed with 100 mg/L ambroxide. Top to bottom is EIC$_{237\ m/z}$ (ambroxide, 2.19 mins) and EIC$_{253\ m/z}$ (hydroxy-ambroxide derivative, 1.46 mins (74% inferred yield)).

DESCRIPTION OF THE PREFERRED EMBODIMENTS

The first aspect of the invention provides a cytochrome P450 enzyme comprising the amino acid sequence set forth in SEQ ID NO: 3, or a variant thereof having an amino acid sequence having at least 95% identity thereto and having CYP450 activity. This aspect of the invention may alternatively be seen as providing a polypeptide having cytochrome P450 activity, and comprising the amino acid sequence set forth in SEQ ID NO: 3 or a sequence with at least 95% identity thereto. In preferred embodiments, the enzyme comprises an amino acid sequence having at least 96%, 97%, 98% or 99% identity to SEQ ID NO: 3. Most preferably the enzyme comprises the amino acid sequence of SEQ ID NO: 3. In some embodiments, the enzyme may consist of the amino acid sequence of SEQ ID NO: 3, or an amino acid sequence having at least 95, 96, 97, 98 or 99% identity thereto. The origin of the enzyme and methods by which it may be obtained are described below. Similarly, variants of the enzyme falling within the invention are described below, including preferred substitutions etc. by which a variant may be obtained.

The enzyme of the invention is isolated relative to its native or natural form. Thus the enzyme is separated from other components with which it is normally associated. For example, the enzyme may normally be present in a microorganism, but in this aspect of the invention, it is separated from at least some components of that microorganism. The isolated enzyme may take the form of an enriched extract in which the enzyme's concentration is increased relative to its concentration in the microorganism or a simple, untreated, extract thereof. In a preferred aspect, the isolated enzyme is the primary component (i.e. majority component) of any solution or suchlike in which it is provided. In particular, if the enzyme is initially produced in a mixture or mixed solution, the enzyme may be separated or purified therefrom. Thus, for instance, if the enzyme is produced using a protein expression system (such as a cellular expression system using prokaryotic (e.g. bacterial) cells, a cell-free, in vitro expression system), the enzyme may be isolated such that it is the most abundant polypeptide in the solution or composition in which it is present, preferably constituting the majority of polypeptides in the solution or composition, and is enriched relative to other polypeptides and biomolecules present in the native production medium. As discussed below, generally the enzyme of the invention is produced using a cellular expression system, in particular by expression in bacterial cells.

In a preferred feature, the enzyme is present, for example in a solution or composition, at a purity of at least 60, 70, 80, 90, 95 or 99% w/w (dry weight) when assessed relative to the presence of other components, particularly other polypeptide components, e.g. in the solution or composition.

A solution of the enzyme may be analysed by quantitative proteomics to identify the extent of purification of the enzyme of the invention, e.g. to assess if it is the predominant component. For instance, 2D gel electrophoresis and/or mass spectrometry may be used. Such isolated molecules may be present in preparations or compositions as described hereinafter. Alternatively, the extent of purification may more simply be assessed by e.g. SDS-PAGE followed by Coomassie staining to check for contaminants/impurities.

The enzyme of the present invention may be isolated or purified using any technique known in the art. For instance, the enzyme may be produced with an affinity tag such as a polyhistidine tag (His tag), a strep tag, a FLAG tag, an HA tag or suchlike, to enable isolation or purification of the molecule by affinity chromatography using an appropriate binding partner, e.g. a molecule carrying a polyhistidine tag may be purified using Ni$^{2+}$ ions. Alternatively, the enzyme may be isolated or purified by e.g. size-exclusion chromatography or ion-exchange chromatography.

As an alternative to production of the enzyme of the invention in a protein expression system, it may be chemically synthesised in a non-biological system, e.g. liquid-phase synthesis or solid-phase synthesis may be used. An enzyme produced by chemical synthesis (i.e. by a non-biological method), by contrast, is likely to be produced in an isolated form. Thus, no specific purification or isolation step is required for an enzyme of the invention to be considered isolated, if it is synthesised in a manner which produces an isolated molecule.

The enzyme may be provided in a solution or in a composition, e.g. with a suitable solution to maintain viability. The enzyme may also be provided in lyophilised form or immobilised or tethered to other macromolecules or support materials such as alginate beads, iron affinity beads, nickel columns and electrochemical electrodes.

A second aspect of the invention provides a nucleic acid molecule comprising a nucleotide sequence encoding the cytochrome P450 enzyme of the invention. Thus the invention provides a nucleic acid molecule comprising a nucleotide sequence encoding a cytochrome P450 enzyme comprising the amino acid sequence set forth in SEQ ID NO: 3, or a variant thereof having an amino acid sequence having at least 95% identity thereto and having CYP450 activity.

It will be appreciated by those of ordinary skill in the art that, as a result of the degeneracy of the genetic code, there are many nucleotide sequences that may encode any given amino acid sequence. By degenerate nucleotide sequences is meant two (or more) nucleotide sequences which encode the same protein (or protein sequence), specifically in the open reading frame of the reference nucleotide sequence which begins at position 1 (i.e. in which codon 1 of the encoding sequence corresponds to positions 1-3 of the reference nucleotide sequence).

The native nucleotide sequence of the cytochrome P450 enzyme of SEQ ID NO: 3 is set forth in SEQ ID NO: 9. Thus in a particular embodiment the nucleic acid molecule of the invention comprises the nucleotide sequence of SEQ ID NO: 9. In another embodiment, the nucleic acid molecule of the invention comprises a nucleotide sequence that is degenerate with SEQ ID NO: 9, e.g. a codon-optimised version of SEQ ID NO: 9. In another embodiment the nucleic acid molecule of the invention comprises a nucleotide sequence that is a variant of SEQ ID NO: 9, having at least 90, 95, 96, 97, 98 or 99% identity to SEQ ID NO: 9. The nucleic acid molecule may comprise or consist of the stated sequence.

The nucleic acid molecule of the invention may be an isolated nucleic acid molecule and may further include DNA or RNA or chemical derivatives of DNA or RNA. The term "nucleic acid molecule" specifically includes single and double stranded forms of DNA and RNA. Methods for isolating or synthesising nucleic acid molecules are well known in the art.

The invention further provides a construct comprising the nucleic acid molecule of the invention. The construct is conveniently a recombinant construct comprising the nucleic acid molecule of the invention. In the construct, the nucleic acid molecule of the invention may be flanked by restriction sites (i.e. nucleotide sequences recognised by one or more restriction enzymes) to enable easy cloning of the nucleic acid molecule of the invention. In the construct of the invention the nucleotide sequence encoding the enzyme of the invention may conveniently be operably linked within said construct to an expression control sequence, which may be heterologous to the nucleic acid molecule, i.e. non-native, meaning that the expression control sequence and nucleic acid molecule are not found together in any native molecule. Such an expression control sequence is typically a promoter, though the nucleotide sequence encoding the enzyme may alternatively or additionally be operably linked to other expression control sequences such as a terminator sequence, an operator sequence, an enhancer sequence or suchlike. Accordingly, the construct may comprise a native or non-native promoter (relative to the nucleic acid molecule), preferably a non-native promoter. The promoter may be constitutive or inducible.

The term "operatively linked" refers to the association of two or more nucleic acid molecules on a single nucleic acid fragment so that the function of one is affected by the other. For example, a promoter is operatively linked to a coding sequence when it is capable of affecting the expression of that coding sequence (i.e. the coding sequence is under the transcriptional control of the promoter). Coding sequences may be operatively linked to regulatory sequences in sense or antisense orientation.

The term "expression control sequence" refers to nucleotide sequences located upstream (5' non-coding sequences), within, or downstream (3' non-coding sequences) of a coding sequence, and which influence transcription, RNA processing or stability, or translation of the associated coding sequence. Expression control sequences may include promoters, operators, enhancers, translation leader sequences, a TATA box, a B recognition element and suchlike. As used herein, the term "promoter" refers to a nucleotide sequence capable of controlling the expression of a coding sequence or RNA. Suitable examples are provided hereinafter. In general, a coding sequence is located 3' to a promoter sequence. Promoters may be derived in their entirety from a native gene, or be composed of different elements derived from different promoters found in nature, or even comprise synthetic nucleotide segments. It is further recognised that since in most cases the exact boundaries of regulatory sequences have not been completely defined, nucleic acid fragments of different lengths may have identical regulatory activity.

Methods for preparing a construct of the invention are well known in the art, e.g. conventional polymerase chain reaction (PCR) cloning techniques can be used to construct the nucleic acid molecule of the invention which may be inserted into suitable constructs (e.g. containing an expression control sequence) using known methods.

The invention further provides a vector comprising a nucleic acid molecule or construct of the invention. The term "vector" as used herein refers to a vehicle into which the nucleic acid molecule or construct of the invention may be introduced (e.g. be covalently inserted) from which the enzyme or mRNA encoding it may be expressed and/or the nucleic acid molecule/construct of the invention may be cloned. The vector may accordingly be a cloning vector or an expression vector.

The nucleic acid molecule or construct of the invention may be inserted into a vector using any suitable methods known in the art, for example, without limitation, the vector and nucleic acid molecule may be digested using appropriate restriction enzymes and then may be ligated with the nucleic acid molecule having matching sticky ends, or as appropriate the digested nucleic acid molecule may be ligated into the digested vector using blunt-ended cloning.

The vector is generally a prokaryotic, specifically bacterial, vector. The nucleic acid molecule or construct of the invention may be produced in or introduced into a general-purpose cloning vector, particularly a bacterial cloning vector, e.g. an *Escherichia coli* cloning vector. Examples of such vectors include pUC19, pBR322, pBluescript vectors (Stratagene Inc.) and pCR TOPO® from Invitrogen Inc., e.g. pCR2.1-TOPO.

The nucleic acid molecule or construct of the invention may be sub-cloned into an expression vector for expression of the enzyme of the invention. Expression vectors can contain a variety of expression control sequences. In addition to control sequences that govern transcription and translation, vectors may contain additional nucleic acid sequences that serve other functions, including for example vector replication, selectable markers etc. Plasmids are preferred vectors according to the invention.

The vector of the invention may further comprise a nucleotide sequence encoding a ferredoxin for use with the enzyme of the invention, as required for the enzyme's cytochrome P450 activity. In a particular embodiment, the vector may comprise a nucleotide sequence encoding the ferredoxin of SEQ ID NO: 4 (SeuF08). The native SeuF08 encoding sequence is set forth in SEQ ID NO: 10. In a particular embodiment, the vector comprises the nucleotide sequence of SEQ ID NO: 10, or a nucleotide sequence degenerate with SEQ ID NO: 10.

When the vector of the invention comprises both a nucleic acid molecule of the invention and a nucleotide sequence encoding a ferredoxin, the two genes may be encoded polycistronically, i.e. within an operon such that expression of both genes is controlled by the same promoter. Alternatively, the two genes may be encoded with separate promoters.

Alternatively or additionally, the vector of the invention may further comprise a nucleotide sequence encoding a ferredoxin reductase (e.g. a ferredoxin-NADP$^+$-reductase) for use with the enzyme of the invention. Preferably the vector comprises nucleotide sequences (i.e. genes) encoding the enzyme of the invention, a ferredoxin and a ferredoxin reductase. The ferredoxin reductase may be encoded as part of an operon with the enzyme of the invention. In a particular embodiment the enzyme of the invention, ferredoxin and ferredoxin reductase are encoded in a single operon. The genes may be encoded in any order within such an operon.

In a particular embodiment the vector encodes the ferredoxin reductase Scf15A. Scf15A has the amino acid sequence set forth in SEQ ID NO: 11. In a particular embodiment, the vector may comprise a nucleotide sequence encoding the ferredoxin reductase of SEQ ID NO: 11. The native Scf15A coding sequence is set forth in SEQ ID NO: 12. In a particular embodiment, the vector comprises the nucleotide sequence of SEQ ID NO: 12, or a nucleotide sequence degenerate with SEQ ID NO: 12.

The invention further provides a microorganism comprising the nucleic acid molecule of the invention, the recombinant construct of the invention or the vector of the invention, wherein the nucleotide sequence encoding the enzyme of the invention is heterologous to the microorganism; or a lysate of such a microorganism. That is to say, the microorganism of the invention does not natively comprise the nucleotide sequence of the nucleic acid of the invention, and more generally the microorganism of the invention does not natively encode or express the cytochrome P450 enzyme of SEQ ID NO: 3. The microorganism is thus not *Streptomyces eurythermus* NRRL 2539. Preferably the microorganism is not *Streptomyces eurythermus*, i.e. it is not any strain of *Streptomyces eurythermus*. The term "lysate" as used herein is interchangeable with "extract".

The microorganism is generally a prokaryote, particularly a bacterium. The bacterium may be a Gram-positive or Gram-negative species or strain, generally a non-pathogenic bacterium. In a preferred embodiment, the bacterium is *Escherichia coli*.

The microorganism may be a cloning host or an expression host. Suitable bacterial expression strains are known, e.g. *E. coli* expression strains, such as *E. coli* (DE3) strains.

A lysate (or extract) of the invention (i.e. a lysate or extract of a microorganism of the invention) comprises the enzyme of the invention. Thus the lysate is a lysate of a microorganism that expresses the enzyme (particularly of a bacterium that expresses the enzyme). Such a lysate or extract may be obtained using standard methods of microorganism cell lysis. For instance, the microorganism may be mechanically lysed (e.g. by French press), acoustically lysed (e.g. by sonication), chemically lysed using an appropriate lysis buffer/reagent (e.g. BugBuster, Sigma Aldrich, USA) or lysed by freeze-thaw. The lysate or extract may be a raw lysate/extract, i.e. subjected to no additional treatment following lysis. Alternatively, the lysate may be processed, e.g. the insoluble fraction may be removed (e.g. by centrifugation) such that only the soluble fraction of the lysate is provided. The resulting soluble fraction may be frozen for later use as described below, or in the preferred embodiment the frozen soluble fraction is lyophilised and preferably the container vessels, e.g. vials containing the resulting lyophilisate, are sealed under vacuum. A lysate (or extract) thus generally encompasses a lysate/extract which has been enriched for the enzyme of the invention relative to the raw lysate/extract.

A further aspect of the invention provides the use of the cytochrome P450 enzyme comprising SEQ ID NO: 3, or a variant thereof having at least 95% identity thereto and having CYP450 activity, for the oxidation of an organic compound. In such uses (and other aspects of the invention) the enzyme is preferably a preferred enzyme of the invention as described herein.

Specifically, and in a preferred aspect, the present invention provides the use of the enzyme cytochrome P450$_{SeuC10}$. This enzyme has the amino acid sequence shown in SEQ ID NO: 3.

The enzyme of the invention and for uses, methods and kits of the invention is present in the strain *Streptomyces eurythermus*, a deposit of which is held by the Mycotoxin Prevention and Applied Microbiology Research Unit, National Center for Agricultural Utilization Research, Peoria, Illinois, United States of America, under the Accession number NRRL 2539. The strain has also been deposited with various other Culture Collection, with the accession numbers ATCC 14975, ATCC 19749, CBS 488.68, DSM 40014, ETH 6677, IFO 12764, IMET 43078, ISP 5014, JCM 4206, JCM 4575, RIA 1030. When this enzyme, or variants thereof, are combined with suitable reductase components, it is able to oxidise organic compounds.

The enzyme cytochrome P450$_{SeuC10}$ can be extracted, with or without purification from the known *Streptomyces eurythermus* NRRL 2539, or other bacterial strain, or similarly extracted, with or without purification from a recombinant expression system via cloning of cytochrome P450$_{SeuC10}$ into an expression system, such as *E. coli*, as will be understood by the skilled person.

Actinomycetes including *Streptomyces eurythermus* NRRL 2539 readily undergo mutation both through natural causes and as a result of artificial treatments such as UV irradiation, radiation treatment and chemical treatment. The present invention embraces all productive mutants of *Streptomyces eurythermus* NRRL 2539. These mutant strains also include any strains obtained by gene manipulation such as gene recombination, transduction and transformation. It is also well-known that the properties of actinomycetes change in some degree even for the same strain after successive cultures. Therefore, strains cannot always be differentiated taxonomically because of a slight difference in culture properties. This invention embraces all strains that can produce the cytochrome P450 enzyme, and especially strains that cannot be clearly differentiated from strain NRRL 2539 or its mutants.

One skilled in the art will appreciate that the present invention can include variants of the particular amino acid sequence which is exemplified herein. Particularly preferred are variants having an amino acid sequence similar to that of the amino acid sequence disclosed herein, in which one or more amino acid residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). The above described substitutions are considered conservative substitutions. Variants include naturally occurring and artificial variants. Artificial variants may be generated using mutagenesis techniques, including those applied to nucleic acid molecules, cells or organisms. Preferably, the variants have substantial identity to the amino acid sequence exemplified herein, as mentioned hereinbefore. As used herein, the term "variant" or "mutant thereof" refers to amino acid sequences which have "substantial identity", preferably having at least 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%,99.5%, 99.6%, 99.1%, 99.8% or 99.9% identity with SEQ ID NO: 3. Desirably, the term "substantial identity" indicates that said sequence has a greater degree of identity with any of the sequences described herein than with prior art amino acid sequences. One can use a program such as the online tool using the CLUSTAL W algorithm (Thompson, J. D., Higgins, D. G. and Gibson, T. J. (1994). Nucleic Acids Research, 22: 4673-4680.) to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applies mutatis mutandis to all amino acid sequences disclosed in the present application. Nucleic acid sequences may be similarly aligned, and their sequence identities calculated, using any suitable programme, e.g. Emboss Needle, e.g. in relation to aspects of the invention concerning nucleic acid sequences.

In a preferred embodiment, the term "variant" generally refers to a sequence having at least 95% identity to SEQ ID NO: 3 and also having CYP450 activity, more preferably at least 96% identity thereto or at least 97% identity thereto, further preferably 98% identity thereto, even more preferably 99% identity thereto, most preferably 100% identity thereto.

A variety of different compounds can be oxidised (e.g. hydroxylated, dealkylated, epoxidated, etc.) using the claimed cytochrome P450 enzyme. In a preferred embodiment, the organic compound to be oxidised will have a rate of conversion to the resulting derivative of at least 3%, more preferably at least 5%, more preferably at least 10%, more preferably at least 25%, more preferably at least 50%, even more preferably at least 70% and most preferably a rate of conversion to the resulting derivative of 100%, using the same conditions described in Example 4 herein.

The compound to be oxidised by the cytochrome P450 enzyme may have an optionally substituted or unsubstituted linear or branched alkyl group, such as methyl, isopropyl or tent-butyl, which is hydroxylated; or an aromatic group, such as an optionally substituted aryl or heteroaryl, which is hydroxylated; or an olefinic group, or substituted aryl or heteroaryl, which is epoxidated; or an alkyl-heteroatom, which is dealkylated.

There is a particularly high conversion rate for these reactions when using the claimed cytochrome P450 enzyme.

Preferably, the compound to be oxidised is of formula I:

where R represents the rest of the compound, and where $R^1$, $R^2$ and $R^3$ are independently selected from H or $C_{1-12}$ alkyl or $C_{6-10}$ aryl, or wherein any two of $R^1$, $R^2$ and $R^3$ may be joined to form an optionally substituted cycloalkyl or heterocycloalkyl or $R^1$, $R^2$ and $R^3$ may be joined together with their bridging carbon to form an olefin, aryl or heteroaryl.

Preferably R is an optionally substituted alkyl; an optionally substituted olefin, an optionally substituted aryl, optionally substituted heteroaryl or optionally substituted heterocycloalkyl.

As used herein "alkyl" means a $C_1$-$C_{10}$ alkyl group, which can be linear or branched or cyclic. Examples include propyl and butyl, pentyl, hexyl, cyclopentyl and cyclohexyl. Preferably, it is a $C_3$-$C_{10}$ alkyl moiety. More preferably it is a $C_5$-$C_6$ alkyl moiety. Preferably the alkyl is an optionally substituted cyclohexyl.

For the avoidance of any doubt, the term cycloalkyl is a cyclic alkyl group.

As used herein "aryl" means an optionally substituted monocyclic, bicyclic or tricyclic aromatic radical, such as phenyl, biphenyl, naphthyl, anthracenyl. Preferably the aryl is an optionally substituted $C_6$ aryl.

As used herein "heteroaryl" means an optionally substituted monocyclic, bicyclic or tricyclic aromatic radical containing at least one and up to four heteroatoms selected from oxygen, nitrogen and sulfur, such as furanyl, pyrrolyl, thiazolyl, isothiazolyl, tetrazolyl, imidazolyl, oxazolyl, isoxazolyl, thienyl, pyrazolyl, pyridinyl, pyrazinyl, pyrimidinyl, indolyl, azaindolyl, isoindolyl, quinolyl, isoquinolyl, triazolyl, thiadiazolyl, oxadiazolyl.

As used herein heterocycloalkyl means an optionally substituted cycloalkyl wherein one to four carbon atoms have been substituted with a heteroatom. Preferably, the heteroatoms are selected from nitrogen, oxygen, sulphur or phosphorous.

As used herein the term "optionally substituted" means an H has been removed from a compound and replaced with an organic fragment such as those comprising a combination of any of carbon, halogen, hydrogen, nitrogen, oxygen and sulphur.

Preferably the compound of formula I has a molecular weight of from 50 to 1000, such as from 100 to 700, more preferably from 200 to 500.

Preferably, $R^1$, $R^2$ and $R^3$ are independently selected from H, $C_{1-6}$ alkyl or $C_{6-10}$ aryl, preferably with the proviso that either one or more of $R^1$, $R^2$ and $R^3$ is H. Most preferably, $R^1$, $R^2$ and $R^3$ are independently selected from H, methyl, ethyl, propyl, butyl, t-butyl, pentyl and hexyl preferably with the proviso that either one or more of $R^1$, $R^2$ and $R^3$ is H.

In a particularly preferred embodiment, the cytochrome P450 enzyme is reacted with a compound such as carbamazepine, bosentan, diclofenac, meloxicam, tivantinib or ambroxide. Other preferred compounds to be used as the substrate are as set out in the Examples, particularly ambroxide, diclofenac, tivantinib, carbamazepine, palmitic acid, BIRB796, vanoxerine, ruxolitinib and perindopril.

The preferred compounds to be oxidised are typically of the following structural formulae:

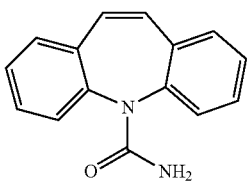

(i)

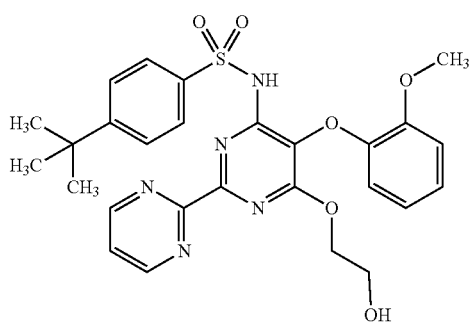

(ii)

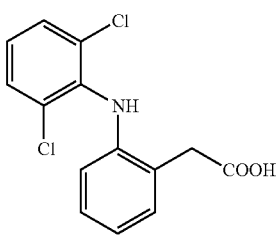

(iii)

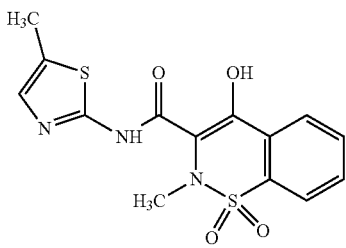

(iv)

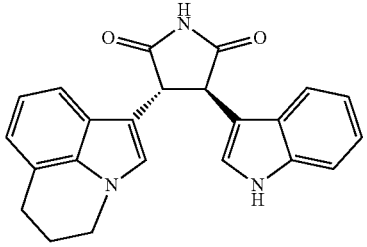

(v)

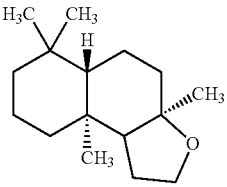

(vi)

The cytochrome P450 enzyme may optionally be used in combination with reductase components, which activate the cytochrome P450. In a preferred embodiment, ferredoxin and ferredoxin reductase components are used. Any components which activate the cytochrome P450 may also be used, including those fused directly or by peptide linkage, or chemical-based oxygen providing surrogates such as peroxide, iodane or chemicals of similar resulting properties. In a particularly preferred embodiment, the enzyme cytochrome P450$_{SeuC10}$ having SEQ ID NO: 3 or a variant thereof having at least 95% identity thereto and having CYP450 activity, is combined with suitable ferredoxin and ferredoxin reductase components to give an effective system to convert a substrate compound to a resulting oxidised derivative.

In a preferred embodiment, the cytochrome P450 enzyme or variant thereof is present in *Streptomyces eurythermus* NRRL 2539 cells.

In another preferred embodiment, the cytochrome P450 enzyme or variant thereof is expressed by at least one recombinant microorganism comprising heterologous nucleic acid encoding the enzyme, derived from *Streptomyces eurythermus* NRRL 2539. As used herein the term "comprising" is intended to mean containing at least the claimed sequence, but may include other sequences. In one embodiment, the recombinant microorganism comprises a heterologous nucleic acid encoding the enzyme or variant thereof. In an alternative embodiment, the recombinant microorganism also comprises a heterologous nucleic acid encoding a reductase agent. "Heterologous" has the meaning as described hereinbefore, i.e. the microorganism does not natively comprise the nucleotide sequence of the nucleic acid of the invention.

In another aspect of the invention, there is provided a method for the production of an oxidised organic compound, comprising reacting the organic compound with a cytochrome P450 enzyme comprising SEQ ID NO: 3 or a variant thereof having at least 95% identity thereto and having CYP450 activity.

The choice of compound to be oxidised is discussed above.

In a preferred embodiment, the enzyme is used to catalyse the oxidation of an alkyl or aryl group.

In a particularly preferred embodiment, the compound to be oxidised is carbamazepine, bosentan, diclofenac, meloxicam, tivantinib or ambroxide, or derivatives thereof or other compounds as described in the Examples and hereinbefore.

Optionally, one or more additional component(s) may be used to activate the cytochrome P450 enzyme. In an embodiment according to the present invention, the cytochrome P450 enzyme of the invention is used in combination with reductase components, preferably with ferredoxin and ferredoxin reductase components.

In an embodiment of the invention, the enzyme is present in a host cell, i.e. a host cell is used for biotransformation of the substrate compound. In a preferred embodiment of the invention, the cytochrome P450 enzyme or variants thereof are present in Streptomyces eurythermus NRRL 2539 cells (i.e. the host cell is a Streptomyces eurythermus NRRL 2539 cell). In another preferred embodiment the host cell is a microorganism of the invention (as described above). The cells may be dosed with the organic compound to be oxidised. The method may optionally comprise an additional step wherein the cells are subsequently harvested and purified (or isolated) to obtain the oxidised compound. In particular, the cells are subsequently harvested and the oxidised compound isolated. That is to say, the method may optionally comprise an additional step in which the oxidised compound is purified (or isolated). In this step the cells are first harvested (e.g. by centrifugation). If the oxidised compound is secreted by the cells, such that it is present in the cell supernatant, the oxidised compound is extracted from the supernatant. Such extraction may be performed using standard methods in the art, as discussed below.

If the oxidised compound is present in the cells, the cells may be lysed (or extracted), e.g. using methods as described above, and the oxidised compound isolated from the lysate. Such isolation may be performed by standard methods in the art, as discussed below.

Culture of the Streptomyces eurythermus NRRL 2539 to produce the P450 enzyme extracts is suitably performed by seeding of a conventional culture medium containing nutrients well-known for use with such microorganisms. Thus, the culture medium contains sources of assimilable carbon and of assimilable nitrogen. The culture medium may also contain inorganic salts. Examples of sources of assimilable carbon include glucose, sucrose, starch, glycerin, millet jelly, molasses and soybean oil. Examples of sources of assimilable nitrogen include soybean solids (such as soybean meal or soybean flour), wheat germ, meat extracts, peptone, corn steep liquor, dried yeast and ammonium salts, such as ammonium sulphate. If required, inorganic salts, such as sodium chloride, potassium chloride, calcium carbonate and various phosphates, may also be included. The medium is preferably sterilized and has a pH adjusted to 5 to 8. Culture of any other bacterial strain or species may similarly be performed in any appropriate medium, as known in the art.

The skilled person will understand that the particular cultivation technique employed is not critical to the invention and any technique commonly used for the cultivation of Actinomycete bacteria (or other types of bacteria as required) may equally be employed with the present invention. In general, the techniques employed will be chosen having regard to industrial efficiency. Thus, liquid culture is generally preferred and the submerged culture method is most convenient from the industrial point of view. Cultivation is preferably carried out under aerobic conditions.

The enzyme of this invention may be produced with an induction agent present. For preference, but not limited to, the induction agent is selected to be the same as the intended substrate for the isolated enzyme. When from 4 hours to 3 days have elapsed after inoculation, preferably 0.05 to 5 mM, more preferably 0.2 mM of induction agent is added, and then cultivation is continued for 2 hours to 1 week, preferably for about one day. The temperature of cultivation is typically 20° C. to 45° C., preferably 25° C. to 30° C., optimally about 27° C. Shake culture or aeration techniques can be adopted.

The cells obtained by the cultivation may be disrupted by cell disruption techniques such as high-pressure homogenisation in buffer solution. The supernatant obtained by centrifugation gives the crude enzyme solution. For example, the enzyme of the present invention can be obtained in a supernatant produced by centrifugation at 38,000×g for 20 minutes.

In an alternative embodiment, the cytochrome P450 enzyme or variants thereof are expressed by at least one recombinant microorganism comprising a heterologous nucleic acid encoding the enzyme (i.e. a heterologous nucleic acid derived from Streptomyces eurythermus NRRL 2539).

Here, the at least one recombinant microorganism can be dosed with an organic compound to be oxidised. This method may optionally comprise an isolation and/or purification step(s) to obtain the oxidised compound, as described above.

In a preferred embodiment, this can be achieved by the recombinant expression of the functional cytochrome P450$_{SeuC10}$ with intact haem. This can be expressed with any or all of the cofactor enzymes. In a particularly preferred embodiment, ferredoxin and ferredoxin reductase may be expressed. This can be achieved by polycistronic plasmid use or via fusion, either via linkers or directly into a single protein product.

Alternatively, the functional cytochrome P450$_{SeuC10}$ protein may be expressed alone without mixing with cofactor enzymes. In a preferred embodiment, cofactor enzymes may be titrated in to provide the active enzyme reaction after material production. The cofactors may be obtained by extraction from wild-type or recombinant materials derived from plants or microbial fermentation. Hussain & Ward, Appl Environ Microbiol. 2003; 69(1):373-382, describe exemplary cloning techniques that may be used.

The native organism, host strain expressing the recombinant enzyme or extracted enzyme is contacted directly with the substrate, preferably in an aqueous medium, either mono or biphasic. Reaction conditions, including choice of pH and temperature will be evident to the skilled person, based on conventional techniques. For example, the reaction may be performed at a pH value in the range of from 5 to 11, more preferably 6.5 to 9.0, most preferably around 8 may be used. To achieve this pH, a selected microbial growth medium or phosphate buffer solution may be used which has the above-mentioned pH. The reaction temperature is preferably within the range from 20° C. to 45° C., more preferably from 25° C. to 30° C. The concentration of the substrate in the reaction medium is preferably within the range from 0.01 to 5.0% by weight. The time allowed for the reaction is normally from 1 minute to 5 days, more usually from 1 day to 5 days, although this may vary, depending upon the concentration of substrate in the reaction mixture, the reaction temperature, and other factors. The extracted enzyme material can either be used directly after extraction, or after storage in frozen solution. In a particularly preferred embodiment, the extracted enzyme material can be dried, preferably by lyophilisation, with or without vessel closure under vacuum, for later use with or without the addition of other components required for reaction, such as other enzyme cofactor components.

After completion of the conversion reaction, the resulting oxidised compound can be isolated (or purified) using conventional procedures, including, for instance, filtration, solvent extraction, chromatography, crystallization, and other isolation procedures. Such procedures will be selected having due regard to the identity of the product. Before, during or after the isolation, the product may or may not be derivatised, as desired. Isolation and purification are referred to herein, in some cases interchangeably. Isolation may be considered a form of purification or the first step of purification, e.g. separation of the cell or oxidised compound from the bulk reaction. Further purification steps may then be conducted to achieve improved purity. Thus reference to isolation herein may be considered a first purification step. Purification may comprise only a first step of isolation, but may also include additional steps to achieve higher levels of purity. Preferably purity levels of at least 80, 85, 90 or 95% w/w (dry weight) are achieved for the oxidised compound.

The starting materials as substrates for the enzyme may be either derived from synthetic routes, naturally occurring, either via natural biomass such as plant material, or produced by fermentation, or by mixed routes thereof. Enzyme reactions can also be performed using pure or non-purified materials, the resulting reaction may be used to aid later purifications of reacted or unreacted components.

Of the substrate compounds used as starting materials, free bases, alkali metal salts, e.g. the sodium or potassium salts, or acid salts of organic or inorganic nature such as tosylate or hydrochlorides, are suitable for use.

After completion of the conversion reaction, the desired compound can be obtained from the reaction system, collected, isolated and purified by conventional means if required, or onward used directly in unpurified form. For example, the reaction product may be centrifuged or filtered and the supernatant or filtrate extracted with a hydrophobic resin, ion-exchange resin or water-immiscible organic solvent such as ethyl acetate. After evaporation of the solvent of the extract, the remaining crude material, for example the remaining crude oxidised compound, may be purified by subjecting it to column chromatography using silica gel or alumina or reversed-phase stationary phase, and by eluting with a suitable eluent. If the starting material is a mixture, then the product can be isolated as a mixture of oxidised compounds which if desired can be separated using chromatography or other suitable techniques.

In general, the resulting oxidised compound may have improved pharmaceutical or agrochemical properties, such as bioactivity potency, improved solubility characteristics, reduced off-target interactions, or simply be of further utility, such as for onward synthesis, or be useful for an analytical standard.

When the cytochrome P450 enzyme preparations of this invention are reacted with substrate compound at pH 8.0 for 5 minutes with (a) ferredoxin, (b) ferredoxin-NADP$^+$-reductase, (c) NADPH regeneration system, and (d) dissolved oxygen, the temperature of reaction ranges at least from 4° C. to 60° C. The optimum pH for each cytochrome ranges from 6.5 to 8.0. Each cytochrome is stable when kept for 24 hours at 4° C. in the pH range between 6.0 and 9.0. Stored lyophilised enzyme is stable at 20-27° C. for 10 days compared to a control stored at <-18° C.

The use of ferredoxin, ferredoxin-NADP$^+$-reductase, oxygen and NADPH is not essential. Any components which can activate the cytochrome P450 may be adopted.

Measurement of the enzyme activity is normally effected in one of two ways:

(i) Measurement on Cytochrome P450:

Measurement is performed according to the method of Omura and Sato et al. (J Biol Chem, 239. 1964, 2370). That is to say, cytochrome P450 is analyzed quantitatively using the following formula, based on the difference in the absorbance of the reduced CO versus the reduced difference spectrum at 450 nm and 490 nm.

$$\text{Cytochrome } P450(\text{mM}) = \frac{\text{Abs}(450 \text{ nm}) - \text{Abs}(490 \text{ nm})}{91(\text{mM cm}^{-1}) \times l(\text{cm})}$$

(ii) Measurement of Rate of Formation of Oxidised Substrate Compound from Substrate Compound The following cocktail of components is employed:

| | |
|---|---|
| Potassium phosphate buffer pH 8.0 | 100 mM |
| MgCl$_2$ | 5 mM |

Enzyme solution containing expressed FdX, FdR, P450 Native concentration when pellet extracted at a rate of 0.30 g cell wet weight per ml extraction buffer

| | |
|---|---|
| NADP$^+$ | 1 mM |
| Glucose-6-phosphate | 5 mM |
| Glucose-6-phosphate dehydrogenase | 1 UN/ml |
| Substrate compound | 0.1 mg/ml |
| Total volume | e.g., 0.1-0.5 ml |

To measure enzyme activity the components of the table are mixed, the solution is shaken at 27° C. for 16-20 hours, and then e.g., 100-500 μl of ACN is added and the reaction stopped. The amount of oxidised substrate formed by the enzyme system is determined with HPLC or UPLC. The reaction may be used on a preparative scale by increasing the volume as appropriate.

In a further aspect, the invention provides a kit comprising:
  i) a cytochrome P450 enzyme comprising SEQ ID NO: 3 or a variant enzyme having at least 95% identity thereto and having CYP450 activity;
  ii) a microorganism that expresses a cytochrome P450 enzyme comprising SEQ ID NO: 3 or a variant enzyme having at least 95% identity thereto and having CYP450 activity, or a lysate of said microorganism; and/or
  iii) a nucleic acid molecule, recombinant construct or vector of the invention as defined above.

Most preferably the kit comprises the cytochrome P450 enzyme of the invention.

If a kit comprises a microorganism or lysate (either fresh, frozen and/or lyophilised) thereof, preferably the microorganism is a microorganism of the invention, as described above, or a lysate of a microorganism of the invention. The kit components, such as the cytochrome P450 enzyme, microorganism or lysate, or nucleic acid molecule, recombinant construct or vector may be lyophilised and/or vacuum sealed.

The kit may further comprise instructions for use for the oxidation of an organic compound. The kit allows the user to screen for the oxidation of compounds of interest.

In a preferred embodiment, the kit further comprises electron donating agents. This is particularly advantageous when the kit comprises the enzyme of the invention. The kit preferably comprises as the electron donating agents a ferredoxin reductase and a ferredoxin with cofactors NADH or NADPH or cofactor regeneration systems such as NAD+ or NADP+, glucose or glucose-6-phosphate, and glucose-dehydrogenase or glucose-6-phosphate dehydrogenase. However, any suitable electron donating agents may be used.

Optionally, the kit may further comprise a buffer, either separately or contained with the other components. This is particularly advantageous when the kit comprises the enzyme of the invention.

Preferably, the kit may further comprise one or more other CYP450 enzymes. This is particularly advantageous when the kit comprises the enzyme of the invention. When the kit comprises a microorganism expressing the enzyme of the invention, the microorganism may further express one or more additional CYP450 enzymes, or the kit may comprise one or more additional microorganisms, or their lysates, each of which expresses a further CYP450 enzyme (i.e. a CYP450 enzyme other than that of the invention). When the kit comprises a nucleic acid molecule, recombinant construct or vector encoding the enzyme of the invention, the nucleic acid molecule, recombinant construct or vector may further encode one or more additional CYP450 enzymes, or the kit may further comprise one or more additional nucleic acid molecules, recombinant constructs or vectors, each of which encodes a further CYP450 enzyme (i.e. a CYP450 enzyme other than that of the invention).

Preferably, the cytochrome P450 enzyme or microorganism or its lysate is lyophilised or immobilised or tethered to other macromolecules or support materials such as alginate beads, iron affinity beads, nickel columns and electrochemical electrodes.

In a further aspect the invention provides a method of producing a cytochrome P450 enzyme of the invention, the method comprising introducing a nucleic acid molecule, recombinant construct or vector of the invention into a microorganism, and expressing the cytochrome P450 enzyme in the microorganism, and optionally purifying (or isolating) the cytochrome P450 enzyme.

Techniques for performing the method are well known in the art. The nucleic acid molecule, recombinant construct or vector may be generated using standard techniques, as described above. The microorganism into which the nucleic acid molecule, construct or vector is introduced is preferably as described above in the context of the microorganism of the invention. That is to say, the microorganism is preferably a bacterium, e.g. E. coli. The enzyme is expressed in the microorganism using standard techniques in the art (e.g. as demonstrated in the Examples below).

To obtain active enzyme the microorganism may be lysed, to provide a lysate comprising the enzyme. Lysis may be performed using standard methods in the art, e.g. French press. The enzyme may then be purified (or isolated), if desired. Purification may be performed using standard methods in the art. For example, the enzyme may be expressed with an affinity tag (e.g. a His tag or a Strep tag) and then purified by affinity chromatography, as described above.

The methods of the present invention are demonstrated in the examples below. These examples are provided as an illustration only and should not be construed as limiting on the present invention.

EXAMPLES

Example 1: Cloning of P450$_{SeuC10}$ from
*Streptomyces eurythermus* NRRL 2539 Extraction
of Genomic DNA from *Streptomyces eurythermus*
NRRL 2539

Genomic DNA (gDNA) was isolated from cell pellet of fermentation material of *Streptomyces eurythermus* NRRL 2539. Culture medium containing 4 g/L yeast extract; 10 g/L malt extract; 4 g/L glucose and adjusted to pH 7.0. Two Erlenmeyer flasks of 250 ml volume, each of which contained 50 ml of the medium, were sterilized 115° C. for 20 minutes. *Streptomyces eurythermus* NRRL 2539 was recovered from cryovial stocks stored in liquid nitrogen and inoculated into the two flasks containing 50 ml of the above growth medium. After 2 days of growth at 27° C. and 200 rpm, 50mls of culture were transferred to 50 ml centrifuge tubes and centrifuged to collect the pelleted cells. The pellet was washed once with an isotonic buffer to remove residual medium components before freezing the pellet at −80° C. for later extraction of genomic DNA as described below. The cell pellet was defrosted and resuspended in 7.5 ml TE buffer (10 mM Tris-HCl pH 7.5, 1 mM Na$_2$EDTA). Seventy-five μl of 20 mg/ml lysozyme solution was added and the solution was incubated at 37° C. for 1 hour, followed by addition of 750 μl of 10% (w/v) SDS and mixing by inverting. After addition of 20 μl of 20 mg/ml pronase and incubation at 37° C. for 1.5 hours, the solution was supplemented with 16 μl of 10 mg/ml RNase solution, followed by another incubation step at 37° C. for 1 hour and 50° C. for 1 hour. Nine hundred μl of 0.5 M NaCl solution was added before the solution was extracted twice with an equal volume of phenol:chloroform:isoamyl-alcohol (25:24:1; Sigma-Aldrich). The aqueous layers were collected and gDNA was precipitated with 1 volume of isopropanol and centrifugation (10,000×g, 30 min, 20° C.). The gDNA pellet was washed once with 100% ethanol and twice with 70% ethanol (~30 ml each wash step). The gDNA pellet was air-dried and resuspended in 5 ml TE buffer. Concentration and purity of the gDNA was measured using a NanoDrop instrument (Thermo Scientific) and gDNA integrity was assessed by agarose gel electrophoresis.

PCR Reactions

The P450$_{SeuC10}$ and ferredoxin$_{SeuF08}$ gene operon (SEQ ID NO: 1) was cloned from *Streptomyces eurythermus* NRRL 2539 in a total reaction volume of 50 μl using primers SeuC10-SeuF08_f (5'-primer sequence-3': ATTTTGTT-TAACTTTAAGAAGGAGATATACATATGAA-GATCGGCACGACGCACC TC) (SEQ ID NO: 5) and SeuC10-SeuF08_r (5'-primer sequence-3': CTACCCGCAGAGGGCGGGGCATAAGCTTCCTATT-AGGCGGAGCGCTCCCGTA CGGTGATG) (SEQ ID NO: 6). PCR reactions contained 10 μl of 5× GC Green buffer (Thermo Scientific), 2.5 μl of DMSO (Sigma), 10 μL of 5 M betaine (Sigma) and 1 μL of formamide (Sigma), 1 μl of 10 mM of dNTPs (Thermo Scientific), 1 unit of HotStart II Phusion® High-Fidelity DNA Polymerase (Thermo Scientific), ~90 ng of genomic DNA, 0.5 μM of each forward and reverse primer and the reaction was filled up to a total volume of 50 µl with MilliQ®-H$_2$O. PCR reactions were performed on an Eppendorf Mastercycler ep Gradient system with the following cycling conditions: 98° C. for 2 minutes, 35 cycles (98° C. for 45 seconds, 72° C. for 30 seconds, 72° C. for 3 minute), 72° C. for 15 minutes. The PCR reaction was analysed by agarose gel electrophoresis and products were extracted from the agarose gel using the Qiagen QIAquick 96 PCR Purification Kit. The concentration of the expected 1558 bp amplicon was measured using the Biochrome Genequant 1300 instrument and on the Molecular Devices Spectramax 384 plus plate reader.

Construction of pHD05 Vector

The pH D05 vector is a derivative of pHD02 (See WO 2018/091885) containing the cer sequence. The cer sequence was amplified from pKS450 plasmid (Summers and Sherratt., EMBO J. 1988; 7(3):851-858.) by PCR using the primers ser_f (5'-primer sequence-3': GGGTCCT-CAACGACAGGAGCACGATCATGCCGGAAATACAG-GAACGCACGCT G) (SEQ ID NO: 7) and ser_r (5'-primer sequence-3': TTATCGCCGGCATGGCGGCCC-CACGGGTGCCGGGGCACAACTCAATTTGCGG GTAC) (SEQ ID NO: 8). The expected 439 bp amplicon was extracted from the agarose gel using the Thermofisher GeneJet Gel Extraction Kit and cloned into the FspAI site of pHD02 by Gibson assembly. The plasmids containing the cer sequence were analysed by PCR screening and DNA sequence was confirmed by Sanger sequencing at LGC Genomics (Germany). The plasmid containing the cer sequence was designated as pHD05.

Figure 2:
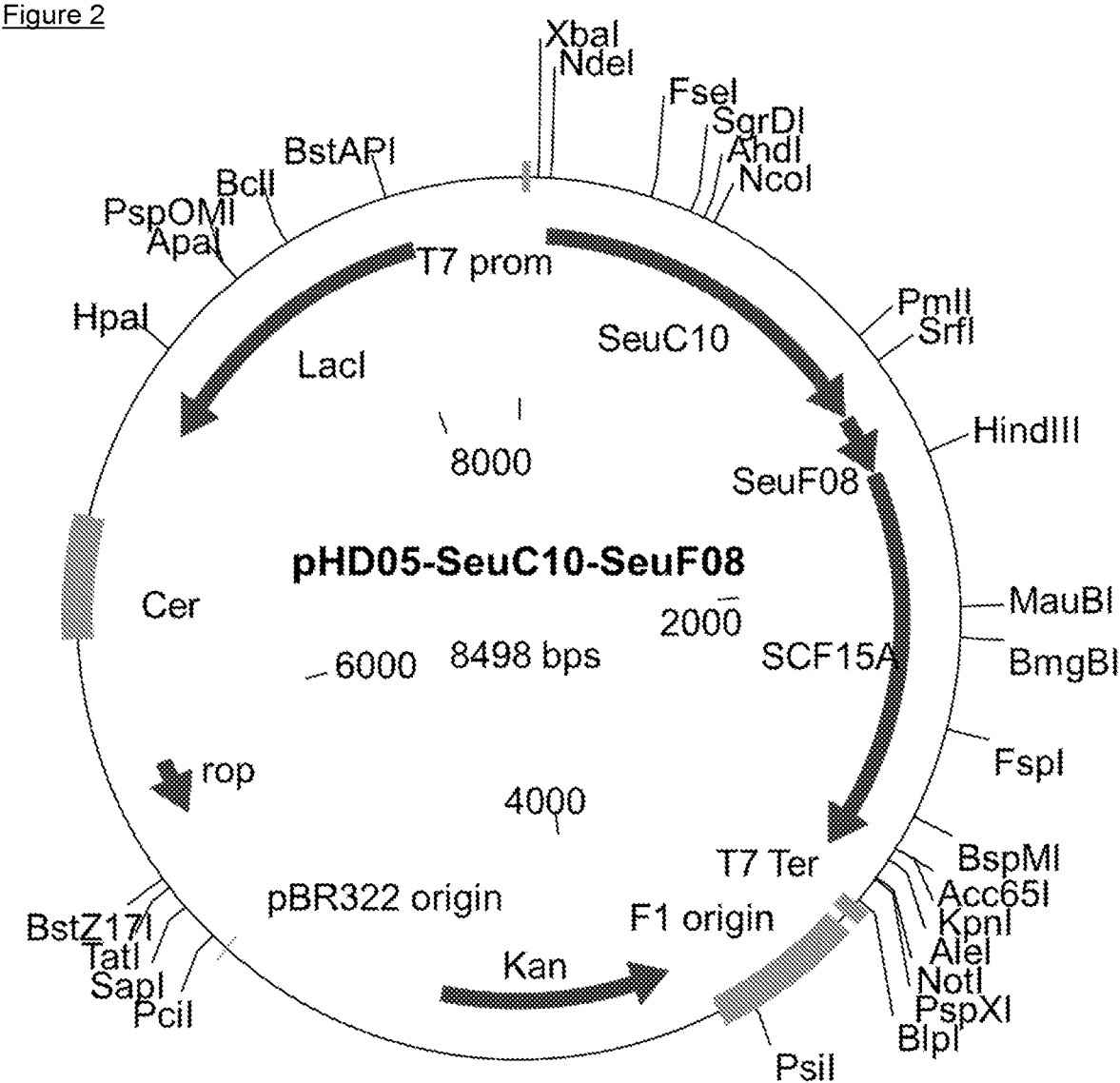
FIG. 2 shows expression plasmid pHD05-SeuC10-SeuF08.

Cloning of the P450$_{SeuC10}$ and ferredoxin$_{SeuF08}$ Gene Operon into pHDO5 Plasmid The purified P450$_{SeuC10}$ and ferredoxin$_{SeuF08}$ amplicon was assembled into pHD05 vector digested with NdeI and EcorI, so that that the cytochrome P450 and ferredoxin gene operon is introduced into a polycistronic operon containing a ferredoxin reductase (scf15a). The vector was digested with restriction endonuclease (New England Biolabs). Restriction digestion was carried out for 16 h at 37° C. in a total volume of 200 µl containing 20 µl of 10× CutSmart buffer®, 4 µl of each restriction endonuclease (40 units; New England Biolabs), ~10.4 µg of plasmid DNA. The reaction was stopped by inactivation of the restriction endonuclease at 65° C. for 20 min. The expected digested products were purified using the Thermo Scientific GeneJET Gel Extraction Kit. The purified digested vector and purified P450 amplicon were assembled together using Gibson assembly in a total volume of 20 µL containing ~50 ng of digested vector and 1:3 (vector:insert) molar concentration of insert, 6.65% PEG 8000, 133 mM Tris-HCl (Fisher), pH7.5, 13.3 mM MgCl$_2$ (Sigma), 13.3 mM DTT (Sigma), 0.266 mM dNTP (New England Biolabs), 1.33 mM NAD (New England Biolabs), 0.495 Unit of Phusion DNA polymerase (New England Biolabs), 79.5 Units of Taq DNA ligase (New England Biolabs) and 0.075 Units of T5 exonuclease (New England Biolabs). The reaction mixture was incubated at 50° C. for 1 hour and 1 µL was introduced into 25 µL of chemically competent cells E. coli DH5a (Invitrogen) by chemical transformation. Clones were selected on Miller's Luria broth (LB) plates containing 50 µg/mL kanamycin after 16 hours of incubation at 37° C. Clones were picked and cultivated in 5 mL LB containing the same antibiotic and recombinant plasmids were isolated from the cultures using the QIAGEN QIAprep 96 Plus Kit. DNA sequences of the P450, ferredoxin and ferredoxin reductase were analysed by PCR screening and DNA sequence was confirmed by Sanger sequencing at LGC genomics (Germany). The constructed plasmid was designated as pHD05-SeuC10-SeuF08 (FIG. 2).

Construction of the Recombinant Expression Strain

The strain E. coli Tuner (DE3) (Merck) was used as a host for recombinant expression of P450$_{SeuC10}$, ferredoxin$_{SeuF08}$ and ferredoxin reductase$_{SCF15A}$. To construct this expression strain, E. coli Tuner (DE3) cells were transformed with the expression plasmid using chemical transformation. Twenty-five µl of chemically competent cells were mixed with 1 µl (~100 ng) of pHD05-SeuC10-SeuF08 plasmid followed by incubation on ice for 30 min. Heat shock was performed at 30 sec in a water bath at 42° C. and cells were subsequently chilled on ice for 2 min. One millilitre of LB was added to the cells and incubated for 1 hour at 37° C. and shaking at 250 rpm. The transformation mixture was plated onto LB plates containing 50 µg/ml kanamycin. Plates were incubated at 37° C. for 16 hours. To prepare glycerol stocks of this expression strain, several colonies were picked with a sterile loop and inoculated into 5 ml LB media containing the same antibiotics and cultivated at 37° C. and 250 rpm for 16 h. Five hundred millilitres of this culture were mixed with 500 µl of 50% (w/v) glycerol in cryovials and stored at −80° C.

Example 2: Expression of recombinant P450$_{SeuC10}$

Preculture: Five milliliters of LB Miller media (Sigma) supplemented with 50 µg/ml of kanamycin was inoculated with a loop scraped from a cryovial containing E. coli Tuner (DE3) harbouring the pHD05-SeuC10-SeuF08 expression plasmid. Cells were grown overnight at 37° C. and 250 rpm in a New Brunswick Scientific Innova 4230 shaking incubator.

Seed: Into a 250 ml baffled flask, 50 ml of PCM8.1 media supplemented with 50 µg/ml of kanamycin was inoculated with the overnight preculture to an OD600 of 0.1 and incubated at 37° C. and 200 rpm until the end of the day.

The components of PCM8.1 were MgSO$_4$ (0.49 gL$^{-1}$), Na$_2$HPO$_4$*7H$_2$O (6.7 gL$^{-1}$), KH$_2$PO$_4$ (3.4 gL$^{-1}$), NH$_4$Cl (2.68 gL$^{-1}$), Na$_2$SO$_4$ (0.71 gL$^{-1}$), arginine (0.2 gL$^{-1}$), histidine (0.15 gL$^{-1}$), lysine (0.2 gL$^{-1}$), phenylalanine (0.2 gL$^{-1}$), serine (0.2 gL$^{-1}$), threonine (0.2 gL$^{-1}$), tryptophan (0.2 gL$^{-1}$), methionine (0.2 gL$^{-1}$), monosodium glutamate (8 gL$^{-1}$), glucose (0.5 gL$^{-1}$), glycerol (10 gL$^{-1}$) and a 1000-fold diluted trace element solution with FeCl$_3$ (81.1 gL$^{-1}$), CaCl$_2$*6H$_2$O (4.38 gL$^{-1}$), MnCl$_2$*4H$_2$O (1.98 gL$^{-1}$), ZnSO$_4$*7H$_2$O (2.88 gL$^{-1}$), CoCl$_2$*6H$_2$O (0.48 gL$^{-1}$), CuCl$_2$*2H$_2$O (0.34 gL$^{-1}$), NiCl$_2$*6H$_2$O (0.48 gL$^{-1}$), Na$_2$MoO$_4$*2H$_2$O (0.48 gL$^{-1}$), Na$_2$SeO$_3$ (0.35 gL$^{-1}$), and H$_3$BO$_3$ (0.12 gL$^{-1}$).

Production: A 1 L baffled flask containing 200 mL of PCM8.1 media supplemented with 50 µg/ml of kanamycin, 23.8 µg/ml of IPTG, 320 µg/ml of 5'-aminolevulinic acid and 55 µg/ml of FeSO$_4$*7H$_2$O was inoculated with the seed cultures to an OD of 0.6. The induced production cultures were incubated at 27° C. and 200 rpm until the cultures had reached stationary phase (approximately 16-20 hours). The cultures were harvested by centrifugation at 3,000 rpm for 15 minutes. The pellets were washed with 30 mL of wash buffer (isotonic 0.85% NaCl with 5% glycerol) and transferred into a fresh 50 mL centrifuge tube. The cells were further centrifuged at 4,000 rpm for 25-35 minutes and the pellet was stored at −20° C. for processing.

Example 3: Extraction & Processing of Enzyme Materials

Suspended cell pellets were provided as described in Example 2, containing recombinant P450, ferredoxin and ferredoxin reductase in 100 mM potassium phosphate buffer pH 8.0, 5 mM $MgCl_2$, 5 mM TCEP, and 1 mM PMSF in a ratio of 3.0 ml of buffer per 1 g of cells. Lysed cells were produced by high pressure disruption using three cycles of 30 kpsi. Lysed material was centrifuged at 38,000×g for 40 minutes (4° C.) and the supernatant was sterilized by passing through a 0.2 micron filter to provide the cell-free enzyme preparation containing recombinant P450, ferredoxin and ferredoxin reductase. The crude extract was then either used immediately for the desired reaction or dispensed into glass vials (typically 0.5 ml per 2 ml vial or 10 ml per 20 ml vial), frozen and lyophilised using an Edwards Supermodulyo Freeze-dryer before being stored in a standard laboratory freezer at −20° C. until required for use.

Figure 3:
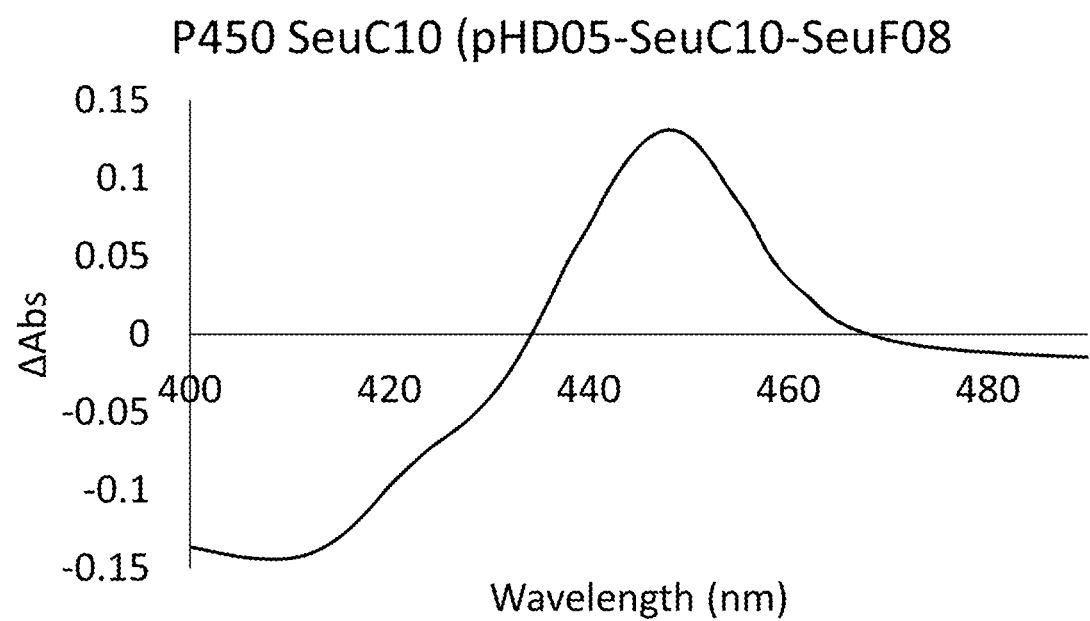
FIG. 3 shows the carbon monoxide difference spectrum of the crude enzyme extract containing P450$_{SeuC10}$ protein. The sample was prepared from IPTG-induced culture of *E. coli* Tuner (DE3) cells containing the pHD05-SeuC10-SeuF08 plasmid.
Figure 4:
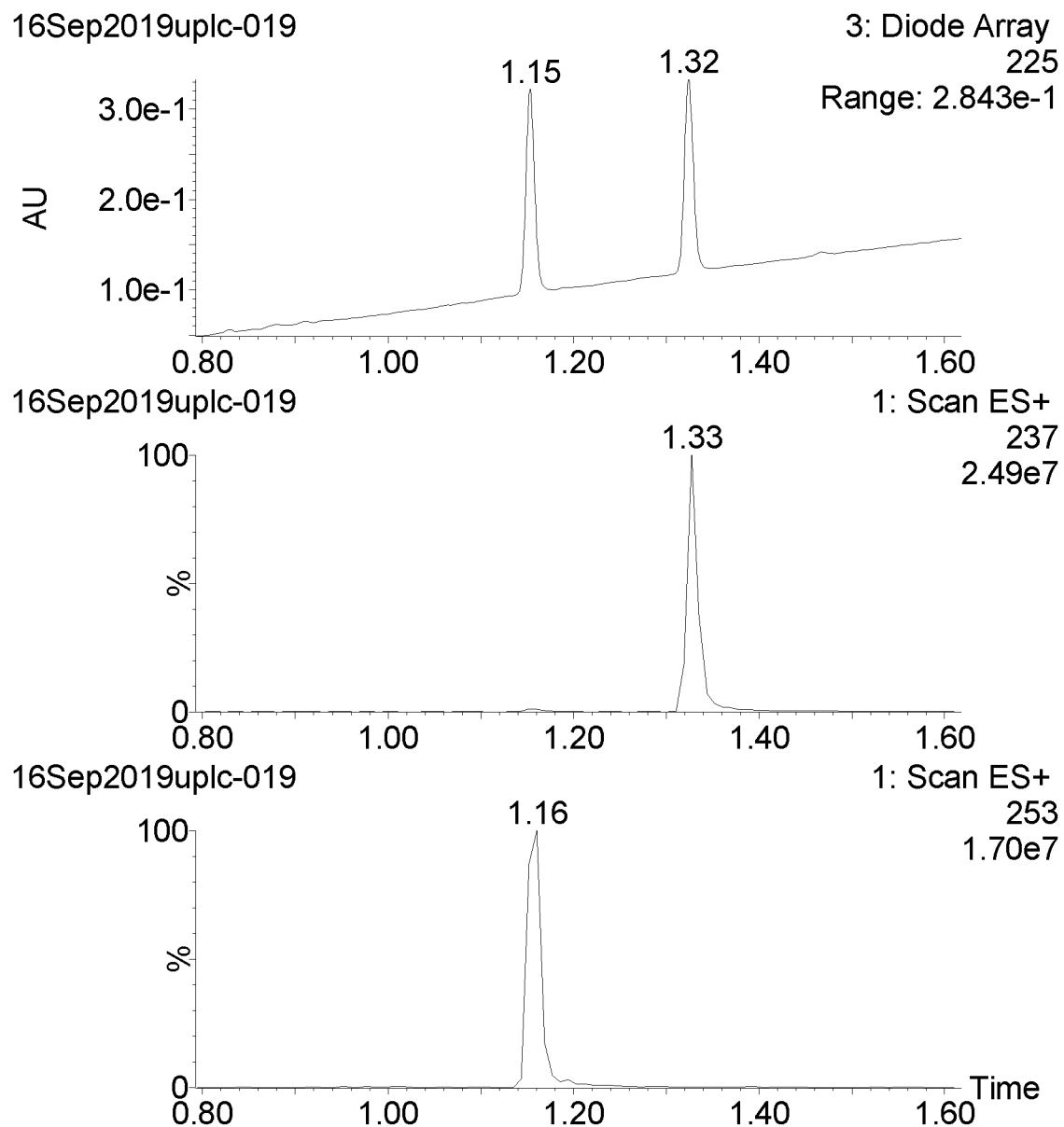
FIGS. 4a-f show UPLC-MS chromatograms of various reactions performed at the 100 μL screening scale.
Figure 4:
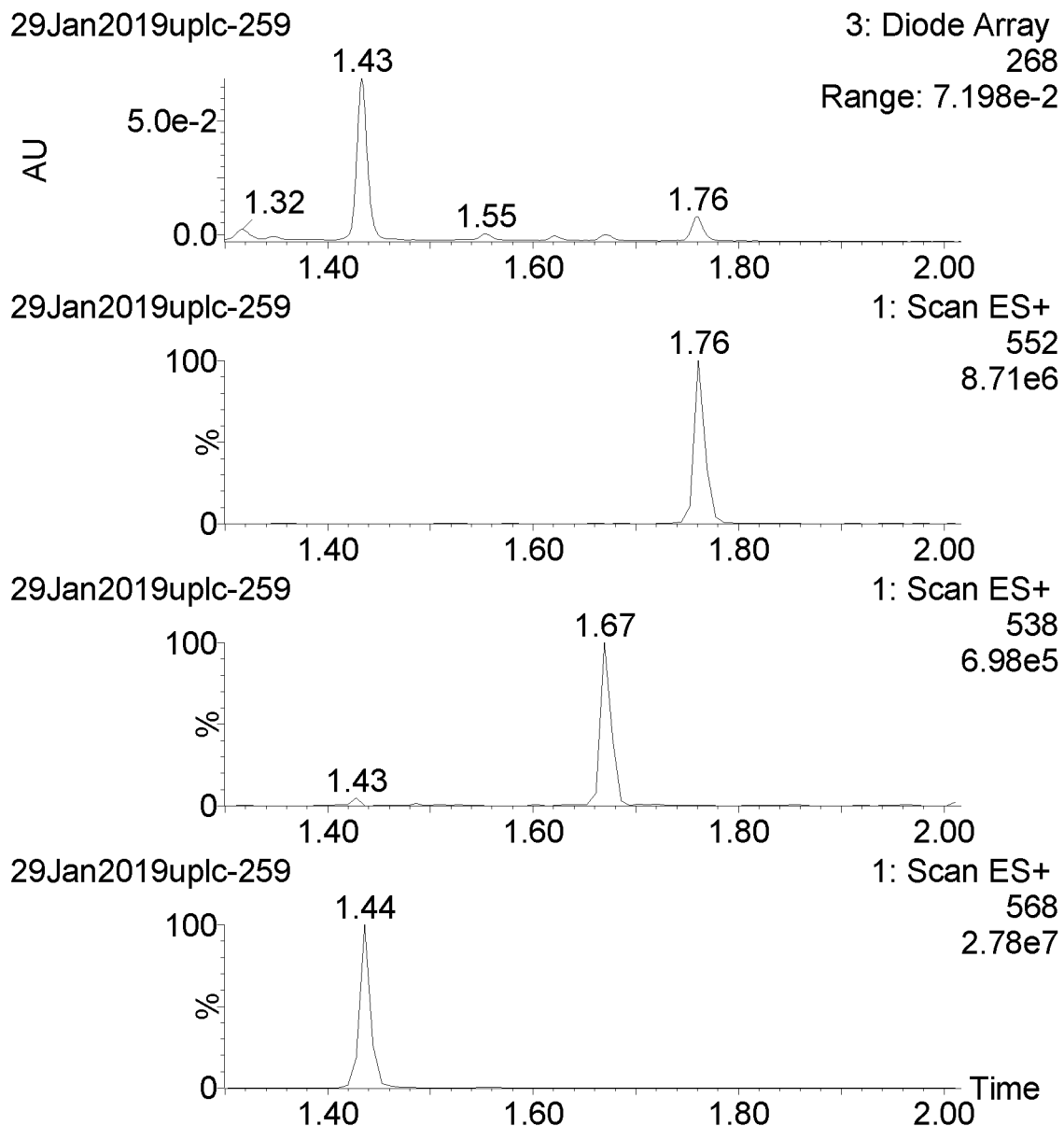
Figure 4:
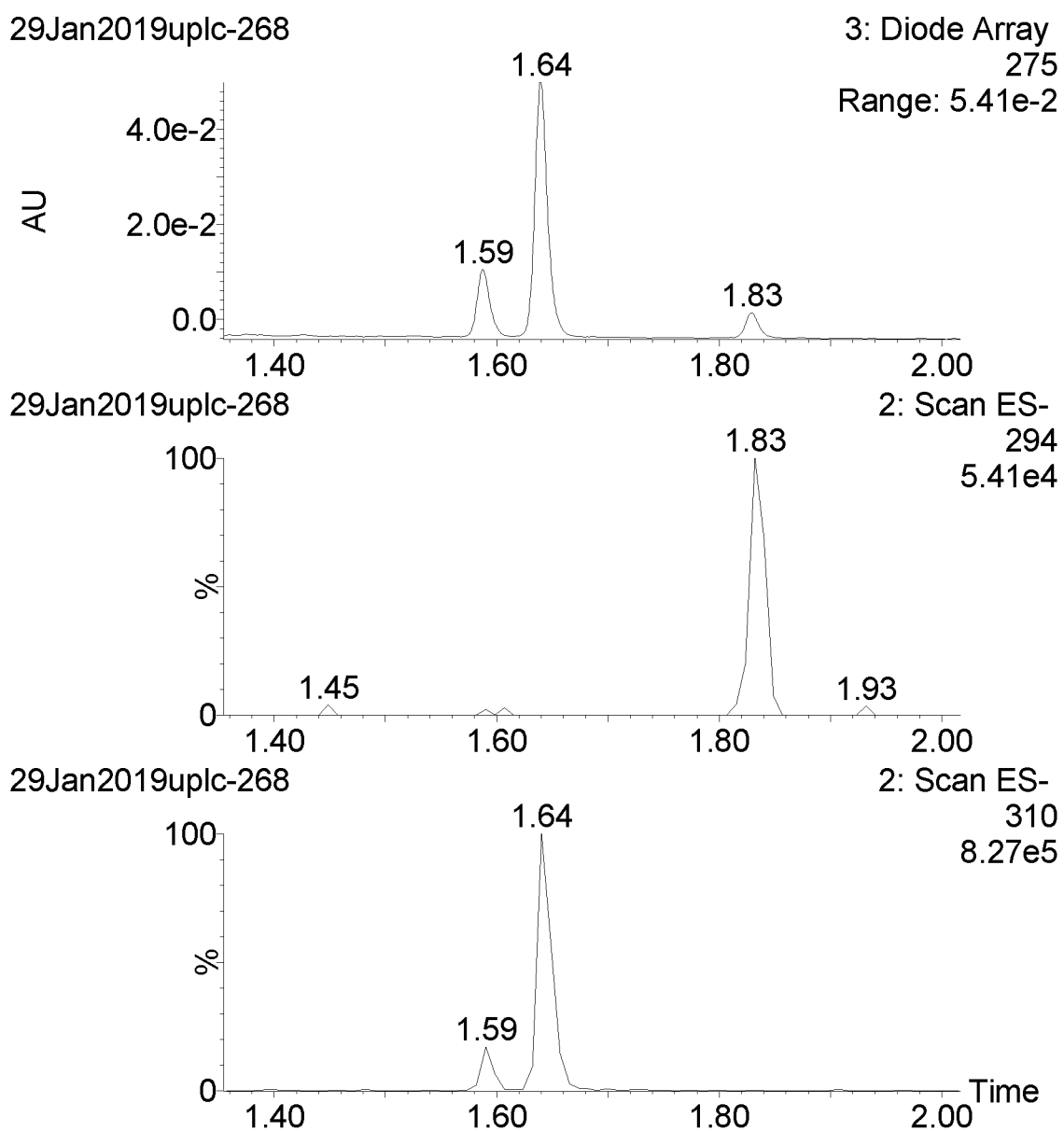
Figure 4:
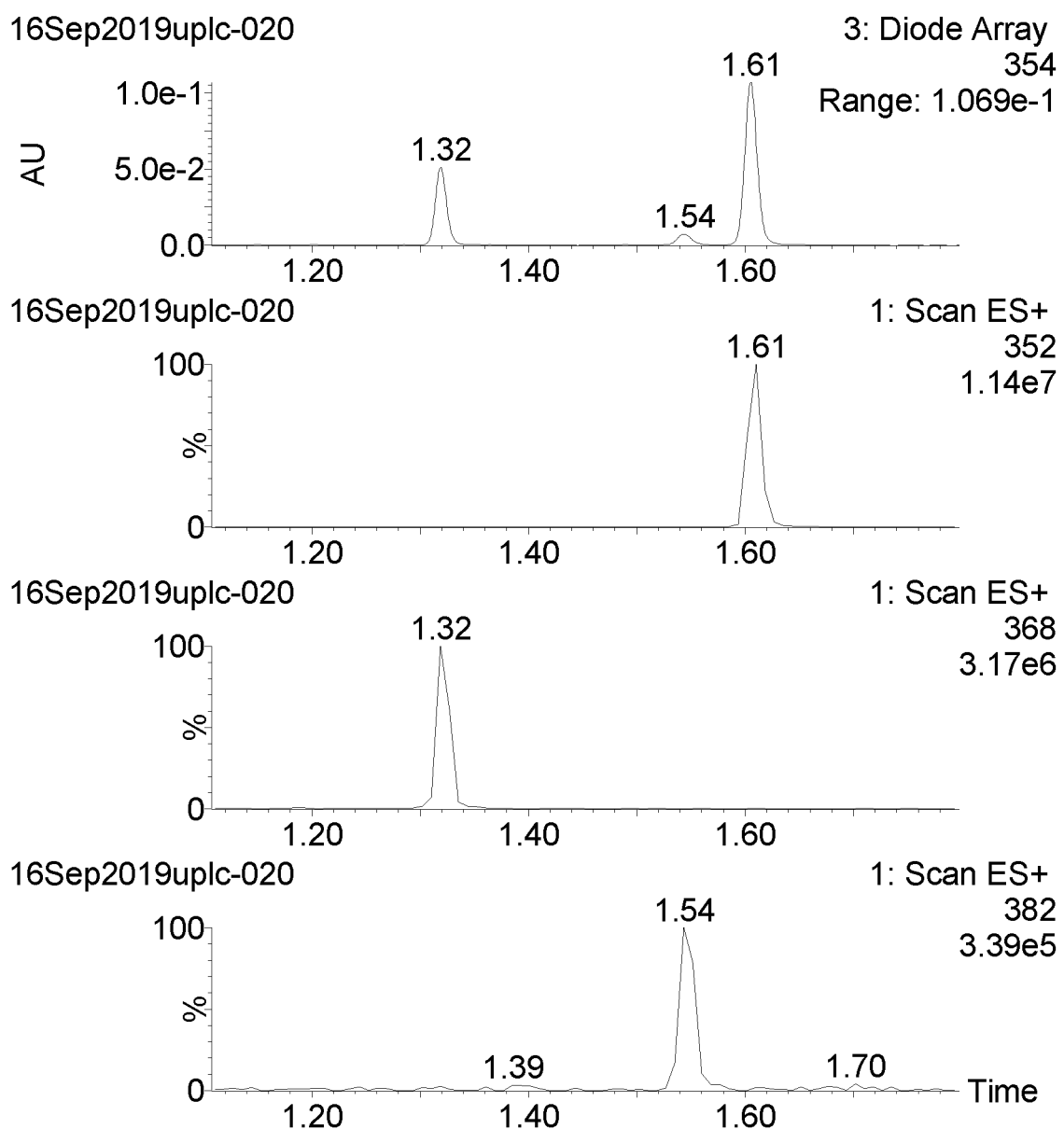
Figure 4:
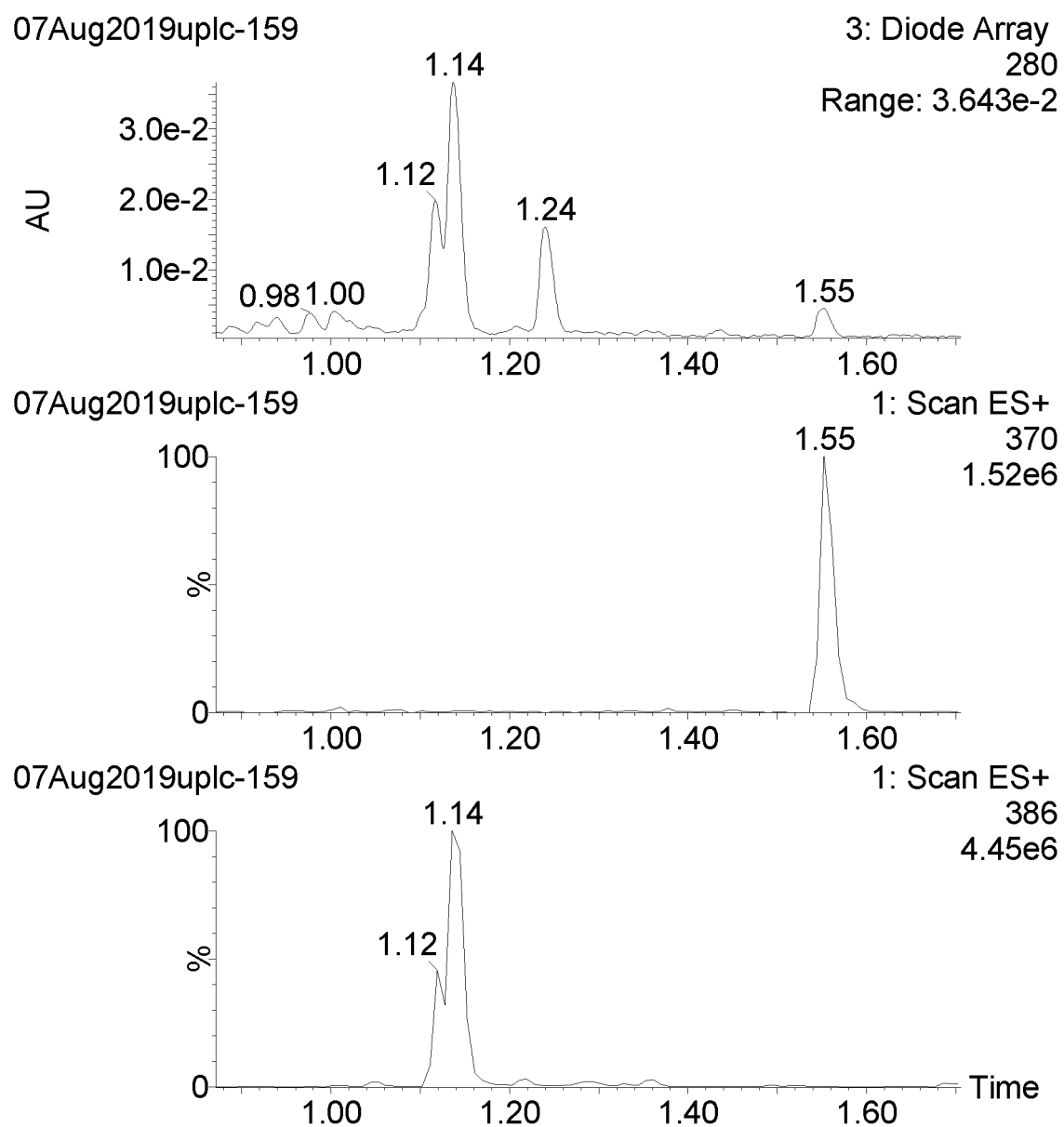
Figure 4F:
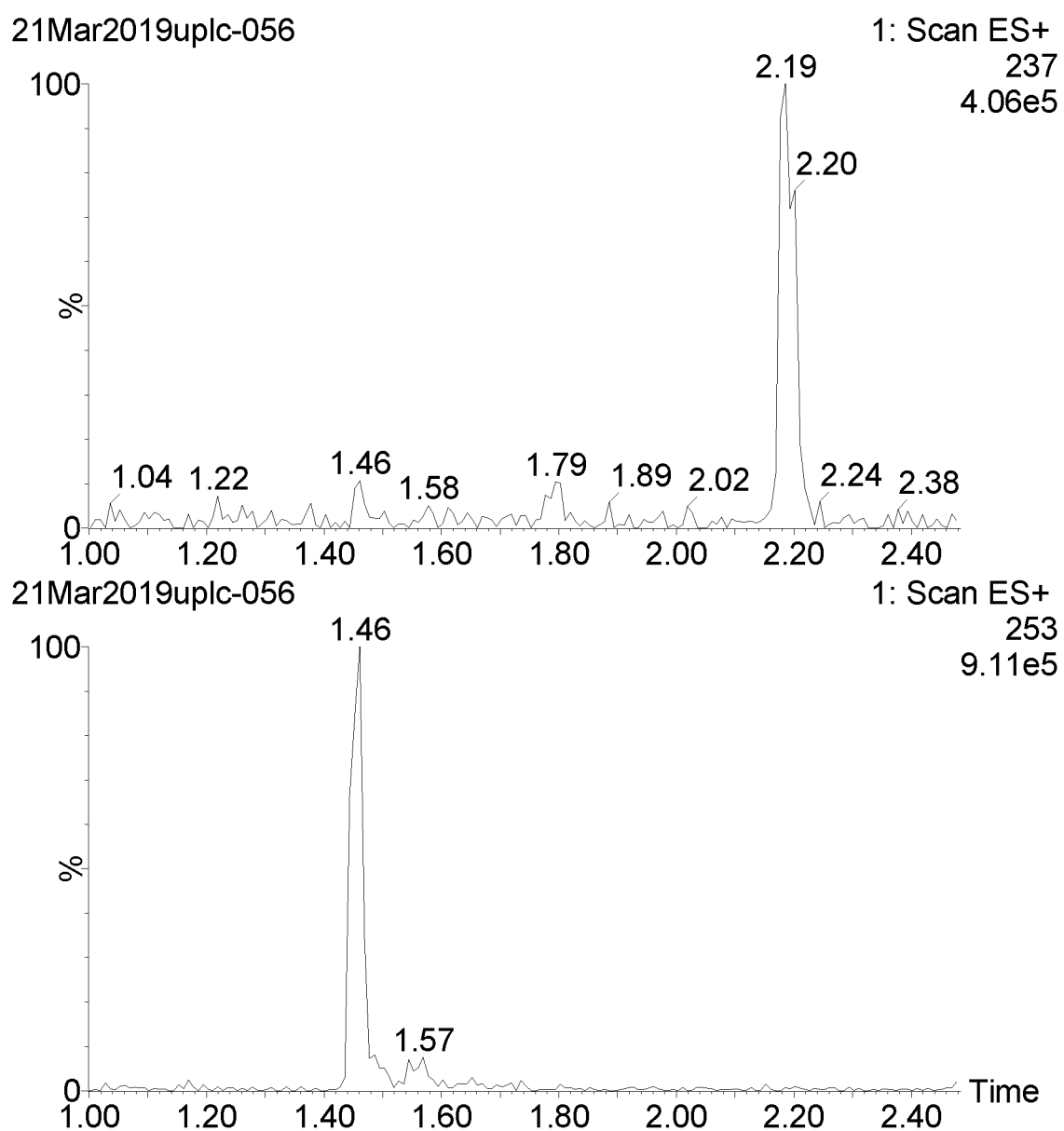

Measurement of the concentration of cytochrome P450 were performed according to the method of Omura and Sato et al. (J. Biol. Chem., 239. 1964, 2370). The cytochrome P450 concentration of cell-free extracts of induced *E. coli* Tuner (DE3) cells harbouring pHD05-SeuC10-SeuF08 was 17 μM. The carbon monoxide difference spectrum for $P450_{SeuC10}$ is shown in FIG. 3.

Example 4A: Oxidase Activity/Spectrum Testing

Lyophilised material of recombinant P450, ferredoxin and ferredoxin reductase proteins was made as described in Example 3 and reconstituted in high purity water to the original volume. Biocatalysis was performed shaking at 27° C. in the following conditions: 100 mM potassium phosphate pH 8.0, 5 mM $MgCl_2$ (both present in the reconstituted enzyme preparation) and 0.1 mg/ml substrate compound such as carbamazepine, bosentan, diclofenac, meloxicam, tivantinib or ambroxide.

Concentrations of P450, ferredoxin and ferredoxin reductase were as extracted (Example 3). Reactions were initiated by addition of 10× stock of cofactor mixture (50 mM G6P, 10 mM NADP, 10 UN/ml G6PDH) to provide a final volume of e.g., 10 μL to 90 μL for 100 μL total reaction volumes. After 16-20 hours, reactions were extracted with an equal volume of acetonitrile, centrifuged to remove precipitated proteins and conversion assessed by UPLC-MS analysis.

UPLC data were obtained as follows:

Column: Acquity UPLC BEH Shield RP18 1.7 μm 2.1 mm i.d. 50 mm length

Solvents: $H_2O$, B: Acetonitrile, both with 0.1% Formic acid

Flow rate: 1.0 ml/min

Detector: Waters Acquity UPLC PDA (UV-Vis detection) and Waters Acquity UPLC QDA (MS)

To confirm the identities of reaction products where known, their chromatographic retention time, mass and ultraviolet spectra were compared with those of authentic metabolite standards.

Representative results for the overall % conversion to oxidised products are shown in Table 1 below.

TABLE 1

Results for substrate testing with lyophilised material containing $P450_{SeuC10}$ co-expressed with $ferredoxin_{SeuF08}$ and ferredoxin $reductase_{SCF15A}$.

| Substrate | Overall % Conversion to Oxidised Products |
| --- | --- |
| Ambroxide | 72.8 |
| Epothilone B | 35.1 |
| Diclofenac | 98.3 |
| Tivantinib | 86.9 |
| Meloxicam | 31.8 |
| Carbamazepine | 49.2 |
| Tolbutamide | 21 |
| Palmitic acid | 70.2 |

Example 4B: Hydroxylase Activity/Spectrum Testing by Whole-Cell Biotransformation in *E. coli*

Cell pellets were provided as in Example 2. The cell pellets were defrosted, washed with 0.85% NaCl buffer and centrifuged at 4,000 RCF, 30 minutes at 4° C. The supernatant was discarded and the pellet was flash frozen in liquid nitrogen. The pellet was allowed to defrost again and resuspended in 40 mL of buffer containing 50 mM potassium phosphate, pH 7.4, 5 mM $MgCl_2$ and 100 mM glucose. Biocatalysis was performed shaking at 27° C. with 0.1 mg/ml substrate compound such as carbamazepine, bosentan, diclofenac, meloxicam, tivantinib, ambroxide or others as shown in Table 2. Reactions were stopped and analysed as in Example 4. Results of wider substrate testing are shown in Table 2, below.

TABLE 2

Results of wider substrate testing for oxidation by $P450_{SeuC10}$ co-expressed in *E. coli* with $ferredoxin_{SeuF08}$ and ferredoxin $reductase_{SCF15A}$.

| Substrate | Overall % Conversion to Oxidised Products |
| --- | --- |
| Ritonavir | 21.6 |
| Buparvaquone | 23.4 |
| BIRB796 | 19.3 |
| Bosentan | 87.1 |
| Vanoxerine | 26.5 |
| Ruxolitinib | 38.6 |
| Perindopril | 14.4 |

Example 5: Comparison of the Activity of $P450_{SeuC10}$ with other Cytochrome P450s Other cytochrome P450 enzymes were expressed as described above, and their activities tested against the same substrates as $P450_{SeuC10}$ using the methods described in Example 4. The other P450s tested were: $P450_{AluC09}$ from *Amycolatopsis lurida* NRRL 2430 (SEQ ID NO: 13, see WO 2018/091885); SriC12 from *Streptomyces rimosus* NRRL 2234 (SEQ ID NO: 14, see WO 2020/109776); SriC20 from *Streptomyces rimosus* NRRL 2234 (SEQ ID NO: 15, see WO 2020/109776); SriC22 from *Streptomyces rimosus* NRRL 2234 (SEQ ID NO: 16, see WO 2020/109776); and CYP107L from *Streptomyces platensis* DSM 40041 (SEQ ID NO: 17, see Worsch et al., Biotechnology and Bioengineering 115: 2156-2166, 2018).

The results are shown in Tables 3 and 4 below, which show the overall % percentage conversion to oxidised products of the substrates. The results reported in Tables 3 and 4, were generated using the methods described in Examples 4A and 4B, respectively, with the substrates as indicated in the tables below. The first column in each table corresponds to the results provided in Tables 1 and 2, above.

TABLE 3

Results for substrate testing with lyophilised material containing the indicated P450

| Substrate | SeuC10 | AluC09 | SriC12 | SriC20 | SriC22 |
|---|---|---|---|---|---|
| Ambroxide | 72.8 | 0 | 0 | 0 | 0 |
| Epothilone B | 35.1 | 46 | 2 | 0 | 0 |
| Diclofenac | 98.3 | 89.9 | 33.9 | 0 | 0.9 |
| Tivantinib | 86.9 | 72 | 27.6 | 2.2 | 9.6 |
| Meloxicam | 31.8 | 25.1 | 73 | 0 | 0 |
| Carbamazepine | 49.2 | 0 | 3.2 | 0 | 0 |
| Tolbutamide | 21 | 0 | 34 | 0 | 0 |
| Palmitic acid | 70.2 | 28.5 | 35.5 | 0 | 0 |

TABLE 4

Results for substrate testing with whole-cells containing the indicated P450

| Substrate | SeuC10 | AluC09 | CYP107L |
|---|---|---|---|
| Ritonavir | 21.6 | 86.3 | 47.5 |
| Buparvaquone | 23.4 | 48.8 | 8.8 |
| BIRB796 | 19.3 | 5.2 | 0 |
| Bosentan | 87.1 | 100 | 93 |
| Vanoxerine | 26.5 | 0 | 7.4 |
| Ruxolitinib | 38.6 | 34.3 | 16.3 |
| Perindopril | 14.4 | 0 | 0 |

As shown in the tables, the enzyme of the invention (SeuC10) demonstrates higher levels of conversions of almost all substrates than any other single cytochrome P450 tested.

The invention claimed is:

1. A microorganism comprising a nucleic acid molecule comprising a nucleotide sequence encoding a cytochrome P450 enzyme comprising the amino acid sequence set forth in SEQ ID NO: 3, or a variant thereof having an amino acid sequence having at least 98% identity thereto and having CYP450 activity, wherein the nucleotide sequence encoding the enzyme is heterologous to the microorganism, or a lysate of said microorganism.

2. The microorganism of claim 1, wherein the microorganism is *Escherichia coli*.

3. A kit comprising:
 a microorganism that expresses a cytochrome P450 enzyme comprising the amino acid sequence set forth in SEQ ID NO: 3, or a variant thereof having an amino acid sequence having at least 98% identity thereto and having CYP450 activity, wherein the microorganism is as defined in claim 1, or a lysate thereof.

4. The kit according to claim 3, wherein the kit further comprises a reducing agent, optionally wherein the kit further comprises a buffer.

5. The kit according to claim 3, further comprising one or more other cytochrome P450 enzymes and/or instructions for using the kit for the oxidation of an organic compound.

6. The kit according to claim 3, wherein the microorganism or lysate is lyophilised and/or vacuum sealed.

7. The microorganism according to claim 1, wherein the nucleic acid molecule is
 a) in a recombinant construct comprising said nucleic acid molecule operatively linked to a heterologous expression control sequence; or
 b) in a vector comprising said nucleic acid molecule or comprising the recombinant construct of a).

8. A kit comprising:
 a microorganism that expresses a cytochrome P450 enzyme comprising the amino acid sequence set forth in SEQ ID NO: 3, or a variant thereof having an amino acid sequence having at least 98% identity thereto and having CYP450 activity, wherein the microorganism is as defined in claim 2, or a lysate thereof.

9. The kit according to claim 8, wherein:
 a) the kit further comprises a reducing agent, optionally wherein the kit further comprises a buffer;
 b) the kit further comprises one or more other cytochrome P450 enzyme and/or instructions for using the kit for the oxidation of an organic compound.

10. The kit according to claim 8, wherein the microorganism or lysate is lyophilised and/or vacuum sealed.

11. The microorganism of claim 1, wherein the microorganism is not *Streptomyces eurythermus*.

12. The kit of claim 4, wherein the reducing agent is a ferredoxin reductase and a ferredoxin.

13. The kit of claim 9, wherein the reducing agent is a ferredoxin reductase and a ferredoxin.

* * * * *